US009717276B2

(12) United States Patent
Brammer et al.

(10) Patent No.: US 9,717,276 B2
(45) Date of Patent: Aug. 1, 2017

(54) AEROSOL DELIVERY DEVICE INCLUDING A POSITIVE DISPLACEMENT AEROSOL DELIVERY MECHANISM

(71) Applicant: R.J. Reynolds Tobacco Company, Winston-Salem, NC (US)

(72) Inventors: David Allan Brammer, Smyrna, GA (US); David Jackson, Gainesville, GA (US); Nigel John Flynn, Flowery Branch, GA (US); Eric T. Hunt, Pfafftown, NC (US); Stephen Benson Sears, Siler City, NC (US); Dennis Lee Potter, Kernersville, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 402 days.

(21) Appl. No.: 14/309,282

(22) Filed: Jun. 19, 2014

(65) Prior Publication Data
US 2015/0117842 A1 Apr. 30, 2015

Related U.S. Application Data

(60) Provisional application No. 61/897,917, filed on Oct. 31, 2013.

(51) Int. Cl.
*A24F 47/00* (2006.01)
*F24H 1/00* (2006.01)
(Continued)

(52) U.S. Cl.
CPC ......... *A24F 47/008* (2013.01); *A61M 11/007* (2014.02); *A61M 15/025* (2014.02);
(Continued)

(58) Field of Classification Search
CPC ..... H05B 3/02; A61M 11/008; A61M 11/042; A61M 11/001; A61M 15/025;
(Continued)

(56) References Cited

U.S. PATENT DOCUMENTS 1,771,366 A 7/1930 Wyss et al.
2,057,353 A 10/1936 Whittemore, Jr.
(Continued)

FOREIGN PATENT DOCUMENTS

AU 276250 7/1965
CA 2 641 869 5/2010
(Continued)

OTHER PUBLICATIONS

David A Henderson; Novel Piezo Motor Enables Positive Displacement Microfluidic Pump; Presented at NSTI Nanotech 2007; 2007 New Scale Technologies, Inc. http://www.newscaletech.com/doc_downloads/Positive_Displacement_Microfluidc_Pump.pdf.
(Continued)

*Primary Examiner* — Shawntina Fuqua
(74) *Attorney, Agent, or Firm* — Womble Carlyle Sandridge & Rice, LLP

(57) ABSTRACT

The present disclosure relates to aerosol delivery devices. The aerosol delivery devices include mechanisms configured to deliver an aerosol precursor composition from a reservoir to an atomizer including a heating element to produce a vapor. An actuator may displace a rod to dispense the aerosol precursor composition to the atomizer. Thereby, the rod may move a piston in a pump housing to dispense the aerosol precursor composition. The atomizer may define a chamber in which the heating element is positioned and at which the aerosol precursor composition is vaporized.

27 Claims, 24 Drawing Sheets

(51) Int. Cl.
*H05B 3/02* (2006.01)
*A61M 15/02* (2006.01)
*A61M 15/06* (2006.01)
*A61M 11/00* (2006.01)
*A61M 16/00* (2006.01)
*A61M 11/04* (2006.01)

(52) U.S. Cl.
CPC .......... *A61M 15/06* (2013.01); *F24H 1/0018* (2013.01); *H05B 3/02* (2013.01); *A61M 11/042* (2014.02); *A61M 2016/0024* (2013.01); *A61M 2205/8206* (2013.01)

(58) Field of Classification Search
CPC .............. A61M 15/06; A61M 15/0065; A61M 15/0023; A61M 19/00; A61M 2016/0024; A61M 2205/8206; A24F 47/008; A24F 47/00; A24F 47/002; F24H 1/0018
See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 5,970,974 A | 10/1999 | Van Der Linden et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1* | 3/2001 | Voges .................. A24F 47/002 128/200.14 |
| 6,196,219 B1 | 3/2001 | Hess et al. |
| 6,234,167 B1 | 5/2001 | Cox et al. |
| 6,501,052 B2 | 12/2002 | Cox et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,311,503 B2 | 12/2007 | Van Lintel et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,156,944 B2 | 4/2012 | Han |
| 8,314,591 B2 | 11/2012 | Terry et al. |
| 8,365,742 B2 | 2/2013 | Hon |
| 8,393,331 B2 | 3/2013 | Hon |
| 8,402,976 B2 | 3/2013 | Fernando et al. |
| 8,490,628 B2 | 7/2013 | Hon |
| 8,499,766 B1 | 8/2013 | Newton |
| 8,528,569 B1 | 9/2013 | Newton |
| 8,550,069 B2 | 10/2013 | Alelov |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |

(56) References Cited

U.S. PATENT DOCUMENTS

| | | |
|---|---|---|
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081623 A1 | 4/2013 | Buchberger |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2016/0037826 A1 | 2/2016 | Hearn et al. |
| 2016/0106154 A1 | 4/2016 | Lord |
| 2018/0114411 | 4/2016 | Buchberger |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2 099 710 | 12/1982 |
| GB | 2469850 | 11/2010 |
| WO | WO 97/48293 | 12/1997 |
| WO | WO 2004/043175 | 5/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2013/128176 | 9/2013 |

OTHER PUBLICATIONS

CurieJet®; Low-Power Micro Pump; Ultra Low-Power Slim Diaphragm MicroPump; document downloaded Jul. 29, 2014 http://downloads.microjet.com.tw/CurieJet/CurieJet_Micropump_Catalog%20Ver.20131220.pdf.

Electroosmotic Pump; Wikipedia; website visited Jul. 29, 2014 http://en.wikipedia.org/wiki/Electroosmotic_pump.

Mp6 Piezoelectric Diaphragm Micropump; website visited Jul. 29, 2014 http://www.servoflo.com/micropumps/mp6.html.

The Lee Company; Electro-Fluidic Systems—Pumps; website visited Jul. 29, 2014 http://www.theleeco.com/electro-fluidic-systems/pumps/pumps.cfm.

Piezoelectric Micro Pumps SDMP—Standard Series—Takasago Fluidic Systems; website visited Jul. 29, 2014 http://www.takasago-fluidics.com/products_pump/transfer/SDMP_Standard/.

AdTech Ceramics; Multi Layer Aluminum Nitride (AIN)—Chattanooga, Tennessee; website visited Jul. 29, 2014 http://www.adtechceramics.com/multi-layer-aluminum-nitride-ain.html.

Microfab Technologies; Dispending Devices; Low and High Temperature Devices; website visited Aug. 7, 2014 http://www.microfab.com/index.php?option=com_content&view=category&layout=blog&id=10&Itemid=10.

International Search Report and Written Opinion of the International Searching Authority for corresponding International Application No. PCT/US2014/062803 mailed Feb. 6, 2015.

* cited by examiner

FIG. 28

```
                    START
                      │
                      ▼
┌─────────────────────────────────────────────────────┐
│ DIRECT AN AIRFLOW FROM A CONTROL BODY THROUGH A     │ 1402
│ CARTRIDGE COMPRISING A RESERVOIR AT LEAST PARTIALLY │
│ FILLED WITH AN AEROSOL PRECURSOR COMPOSITION        │
└─────────────────────────────────────────────────────┘
                      │
                      ▼
┌─────────────────────────────────────────────────────┐
│ DISPENSE THE AEROSOL PRECURSOR COMPOSITION FROM THE │ 1404
│ RESERVOIR TO AN ATOMIZER COMPRISING A HEATING       │
│ ELEMENT WITH A POSITIVE DISPLACEMENT APPARATUS      │
└─────────────────────────────────────────────────────┘
                      │
                      ▼
┌─────────────────────────────────────────────────────┐
│ HEAT THE AEROSOL PRECURSOR COMPOSITION DISPENSED    │ 1406
│ FROM THE RESERVOIR WITH THE HEATING ELEMENT TO      │
│ PRODUCE AN AEROSOL                                  │
└─────────────────────────────────────────────────────┘
                      │
                      ▼
                    END
```

FIG. 29

AEROSOL DELIVERY DEVICE INCLUDING A POSITIVE DISPLACEMENT AEROSOL DELIVERY MECHANISM

CROSS-REFERENCE TO RELATED APPLICATIONS

This application claims the benefit of U.S. Provisional Application No. 61/897,917; filed Oct. 31, 2013, which is incorporated herein by reference in its entirety.

FIELD OF THE DISCLOSURE

The present disclosure relates to aerosol delivery devices, such as smoking articles; and more particularly, to aerosol delivery devices that utilize electrically generated heat for the production of aerosol (e.g., smoking articles commonly referred to as electronic cigarettes). Aerosol delivery devices including mechanisms for delivery of an aerosol precursor composition to an atomizer are provided. The smoking articles may be configured to heat an aerosol precursor, which incorporates materials may be made or derived from tobacco or otherwise incorporate tobacco, capable of vaporizing to form an incapable aerosol for human consumption.

BACKGROUND

Many smoking devices have been proposed through the years as improvements upon, or alternatives to, smoking products that require combustion tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robin son et al. And U.S. Pat. Pub. Nos. 2013/0255702 to Griffith, Jr. Et al. and 2014/0096781 to Sears et al., which are incorporated herein by reference. See also, for example, the various types of smoking articles, aerosol delivery devices and electrically powered heat generating sources referenced by brand name and commercial source in U.S. patent application Ser. No. 14/170,838, filed Feb. 3, 2014, to Bless et al., which is incorporated herein by reference.

However, it may be desirable to provide aerosol delivery devices with enhanced functionality. In this regard, it may be desirable to improve delivery of an aerosol precursor composition to an atomizer.

BRIEF SUMMARY OF THE DISCLOSURE

The present disclosure relates to aerosol delivery systems. Such systems have the ability to generate aerosol as a result of heat generated by electrical power sources, and to deliver aerosol that is intended to be drawn into the mouth of a user. Of particular interest are aerosol delivery systems that provide components of tobacco in an aerosol form, such as is provided to smokers by devices commonly known or characterized as electronic cigarettes. As used herein, the term "aerosol" is meant to include vapors, gases and aerosols of a form or type suitable for human inhalation, whether or not visible, and whether or not of a form that might be considered to be "smoke-like."

Various embodiments of mechanisms for delivering an aerosol precursor composition to an atomizer are provided. These mechanisms may include pumps, passively puff-induced delivery of the aerosol precursor composition, pressurized aerosol precursor reservoirs, bubble jet heads, and other mechanisms as described hereinafter.

In one aspect an aerosol delivery device is provided. The aerosol delivery device may include a control body, a cartridge including a reservoir at least partially filled with an aerosol precursor composition, the cartridge being configured to receive an airflow from the control body, a positive displacement apparatus configured to dispense the aerosol precursor composition from the reservoir, and an atomizer including a heating element configured to heat the aerosol precursor composition received from the reservoir to add a vapor to the airflow and form an aerosol.

In some embodiments the positive displacement apparatus may include an actuator, a piston, and a pump housing. The actuator may be configured to displace the piston within the pump housing to dispense the aerosol precursor composition from the reservoir. In some embodiments the reservoir may define the pump housing. In other embodiments the pump housing may be provided as a separate component in addition to the reservoir. The piston may be configured to displace a fluid from the pump housing into the reservoir. The reservoir may include an aerosol precursor bag.

In some embodiments the actuator may be configured to move the piston in a first direction to draw the aerosol precursor composition from the reservoir into the pump housing. Further, the actuator may be configured to move the piston in an opposing second direction to direct the aerosol precursor composition from the pump housing to the atomizer. The aerosol delivery device may additionally include a valve assembly configured to be positioned between the pump housing and the reservoir.

In some embodiments the atomizer may additionally include a fluid delivery tube configured to deliver the aerosol precursor composition to the heating element. A groove may be defined in an end of the fluid delivery tube. The groove may be configured to receive the aerosol precursor composition. The heating element may define at least one of a size, a shape, and a pattern that substantially matches the groove.

In some embodiments the atomizer may further comprise at least one of a heater disk and a cap. The heating element may be coupled to, imbedded in, or printed on the heater disk or the cap. The heating element may define a tubular configuration. The atomizer may further comprise a fluid delivery tube that is adjacent to and co-linear with the tubular heating element. The atomizer may define a chamber and the heating element may be positioned within the chamber. The aerosol delivery device may include at least two one-way valves opening in opposing directions to alternatively allow the aerosol precursor composition out of the reservoir and into the atomizer.

In a further aspect an aerosol delivery device is provided. The aerosol delivery device may include a cartridge that includes a base and a reservoir at least partially filled with an aerosol precursor composition, and a control body including a coupler. The base and the coupler may be configured to direct the aerosol precursor composition from the reservoir therethrough to an atomizer comprising a heating element configured to heat the aerosol precursor composition received from the reservoir to form a vapor.

In some embodiments the control body may additionally include an electrical power source. Further, the base and the coupler may be configured to form an electrical connection therebetween. The cartridge may be configured to receive an airflow from the control body through the coupler and the base. The aerosol delivery device may additionally include a positive displacement apparatus configured to dispense the aerosol precursor composition from the reservoir through the base and the coupler to the atomizer.

In an additional aspect a method for aerosolization in an aerosol delivery device is provided. The method may include directing an airflow from a control body through a cartridge comprising a reservoir at least partially filled with an aerosol precursor composition, dispensing the aerosol precursor composition from the reservoir to an atomizer comprising a heating element with a positive displacement apparatus, and heating the aerosol precursor composition dispensed from the reservoir with the heating element to produce an aerosol.

In some embodiments dispensing the aerosol precursor composition may include displacing a piston within a pump housing with an actuator. Displacing the piston within the pump housing may include displacing the piston within the reservoir in embodiments in which the reservoir defines the pump housing. In other embodiments displacing the piston within the pump housing may include displacing a fluid from the pump housing into the reservoir. Displacing the fluid from the pump housing into the reservoir may include displacing the aerosol precursor composition from an aerosol precursor bag in the reservoir. Displacing the piston within the pump housing may include moving the piston in a first direction to draw the aerosol precursor composition from the reservoir into the pump housing and moving the piston in an opposing second direction to direct the aerosol precursor composition from the pump housing to the atomizer. The method may additionally include preventing flow of the aerosol precursor composition from the atomizer to the pump housing and preventing flow of the aerosol precursor composition from the pump housing to the reservoir with a valve assembly.

In some embodiments dispensing the aerosol precursor composition from the reservoir to the atomizer may include delivering the aerosol precursor composition through a fluid delivery tube to the heating element. Delivering the aerosol precursor composition through the fluid delivery tube to the heating element may include delivering the aerosol precursor composition to a groove defined in an end of the fluid delivery tube. Heating the aerosol precursor composition may include heating the aerosol precursor composition in the groove. Additionally, heating the aerosol precursor composition may include heating the aerosol precursor composition in a chamber.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE FIGURES

Figure 1:
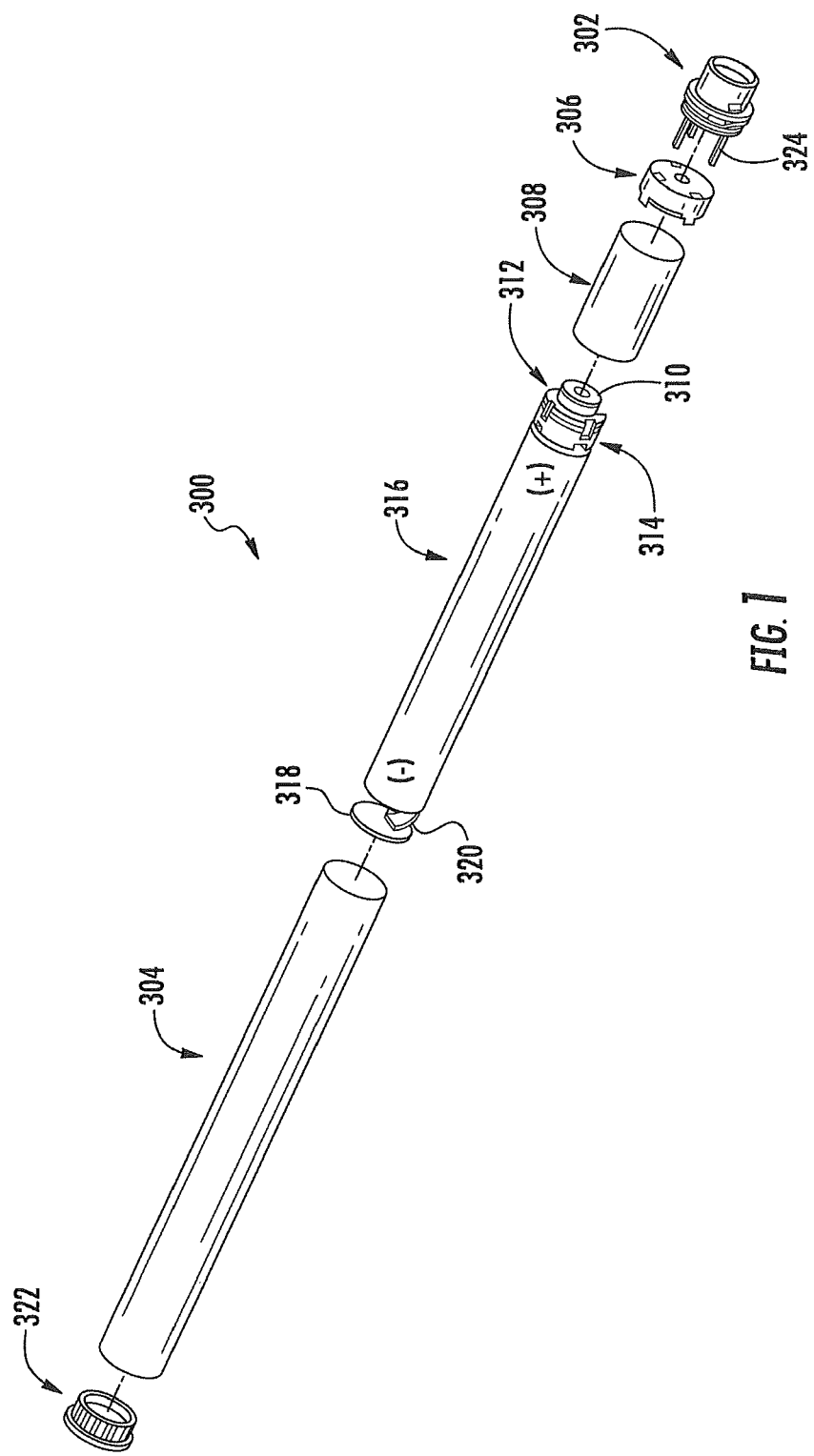
Figure 2:
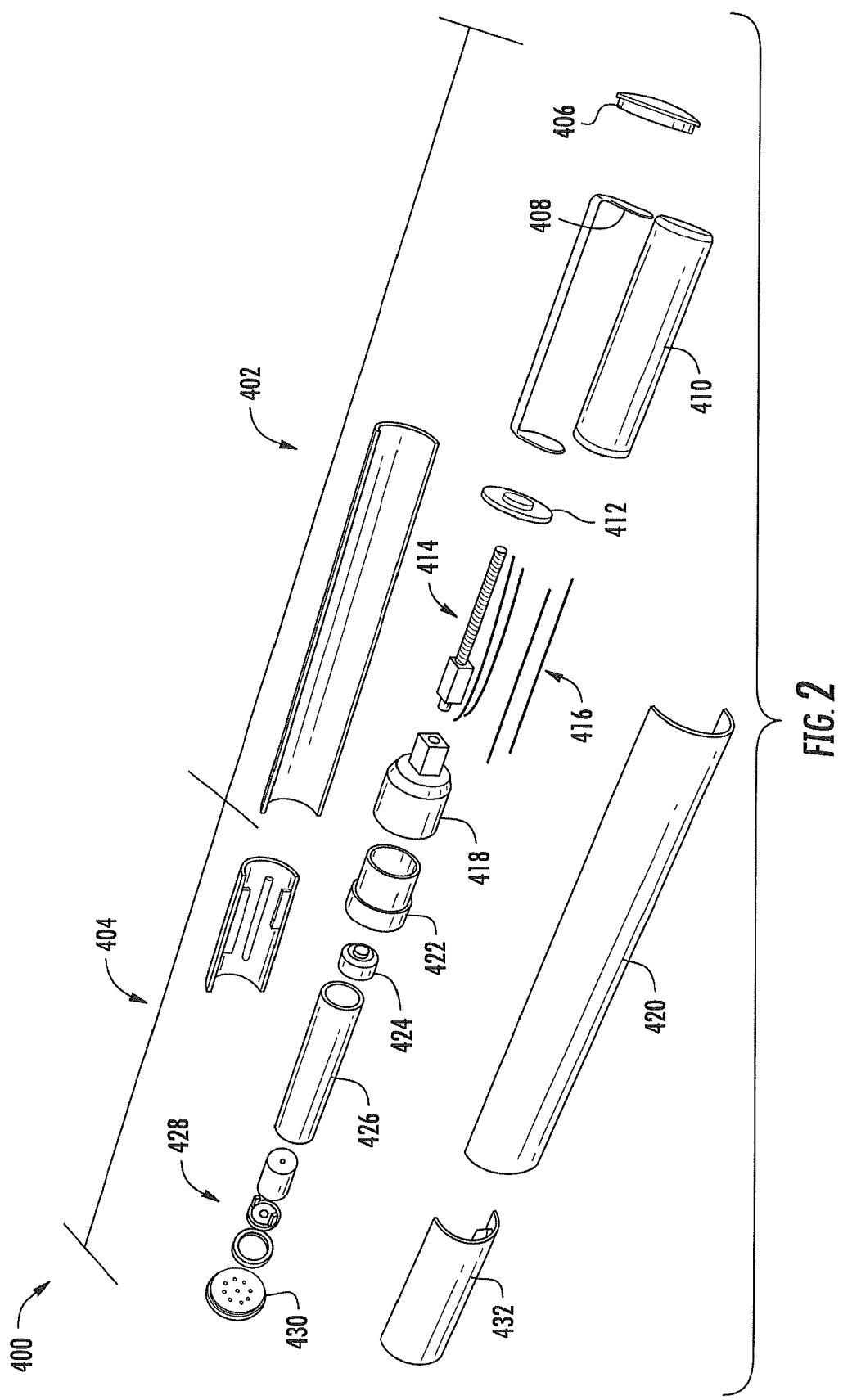
Figure 3:
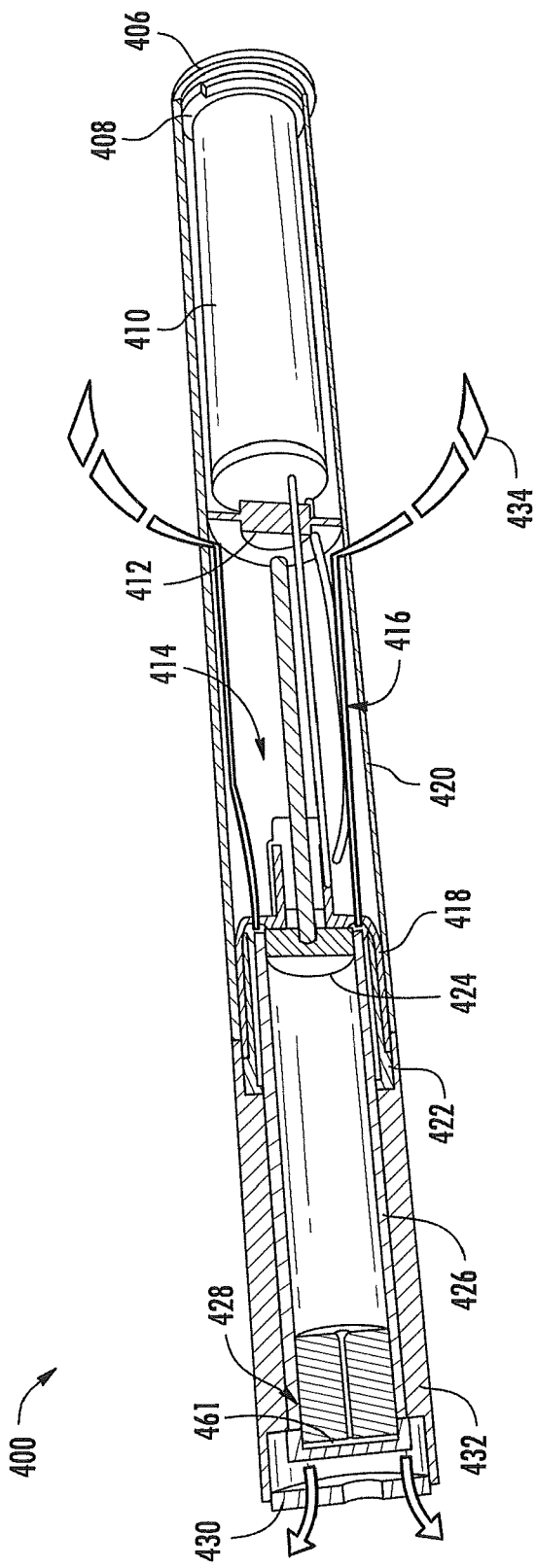
Figure 4:
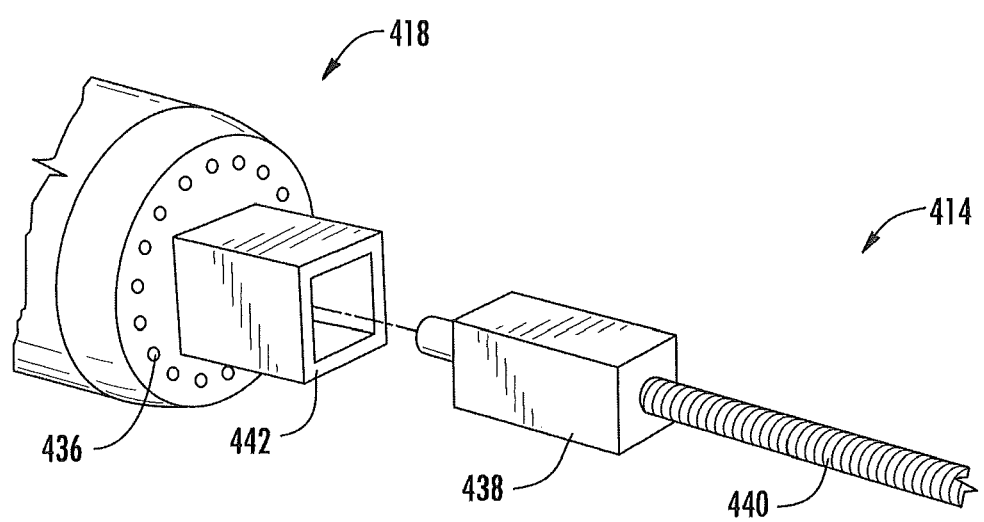
Figure 5:
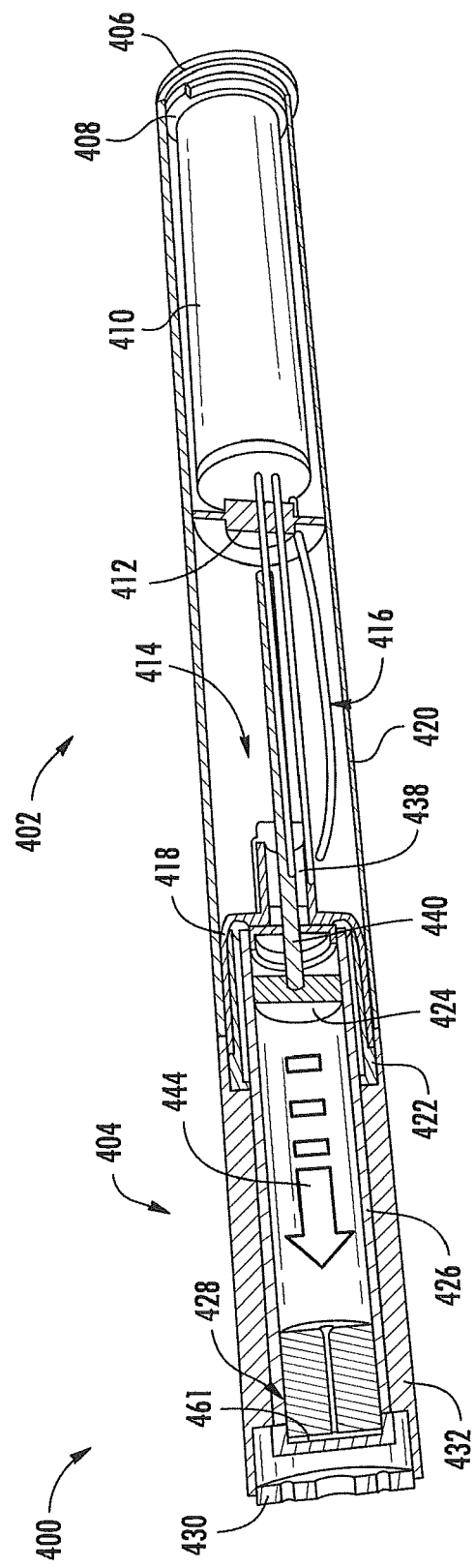
Figure 6:
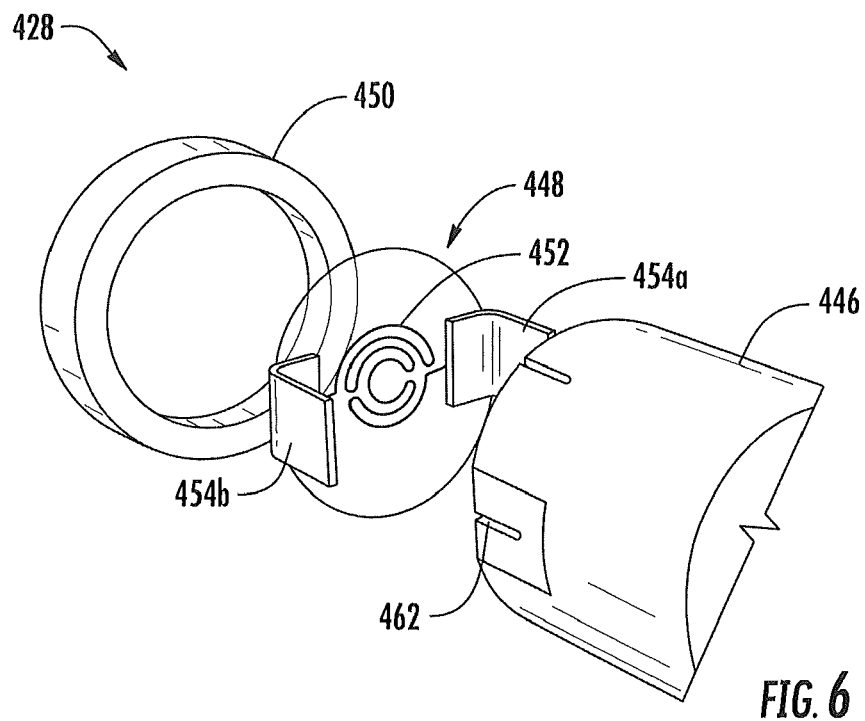
Figure 7:
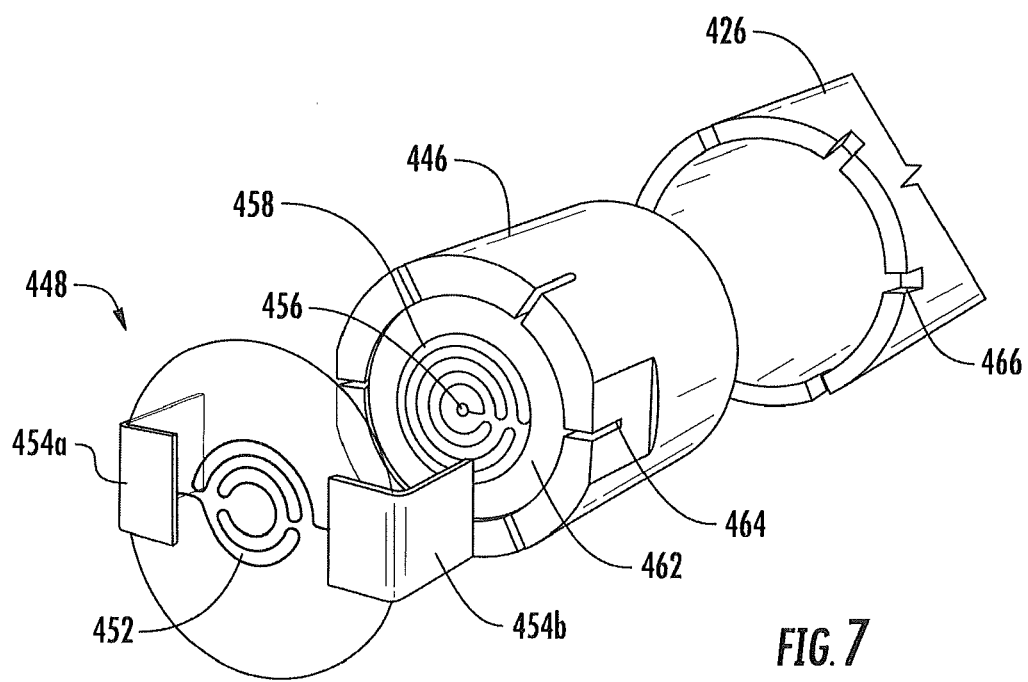
Figure 8:
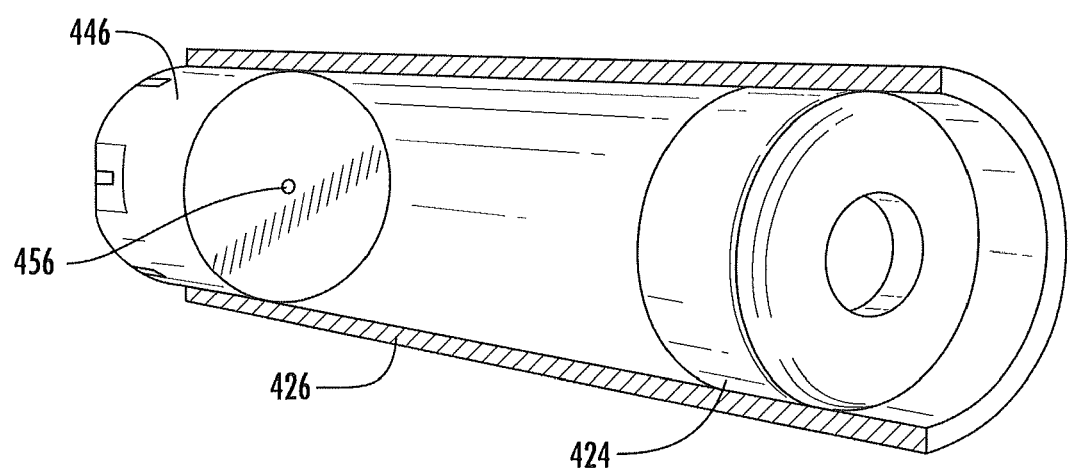
Figure 9:
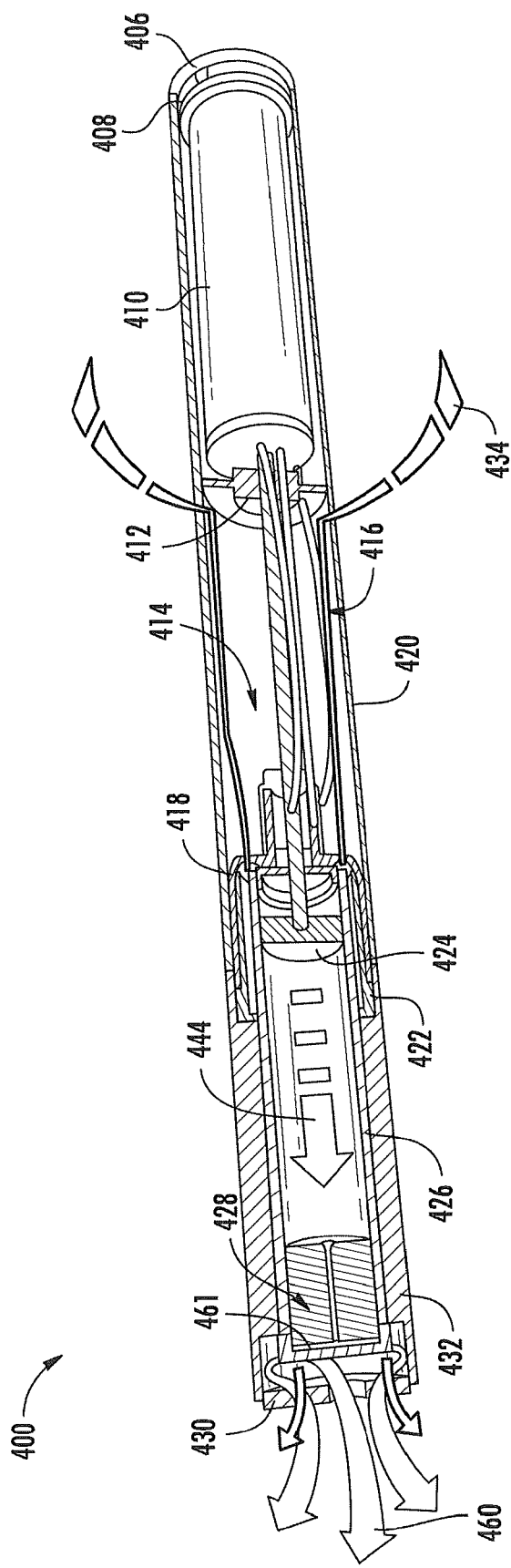
Figure 10:
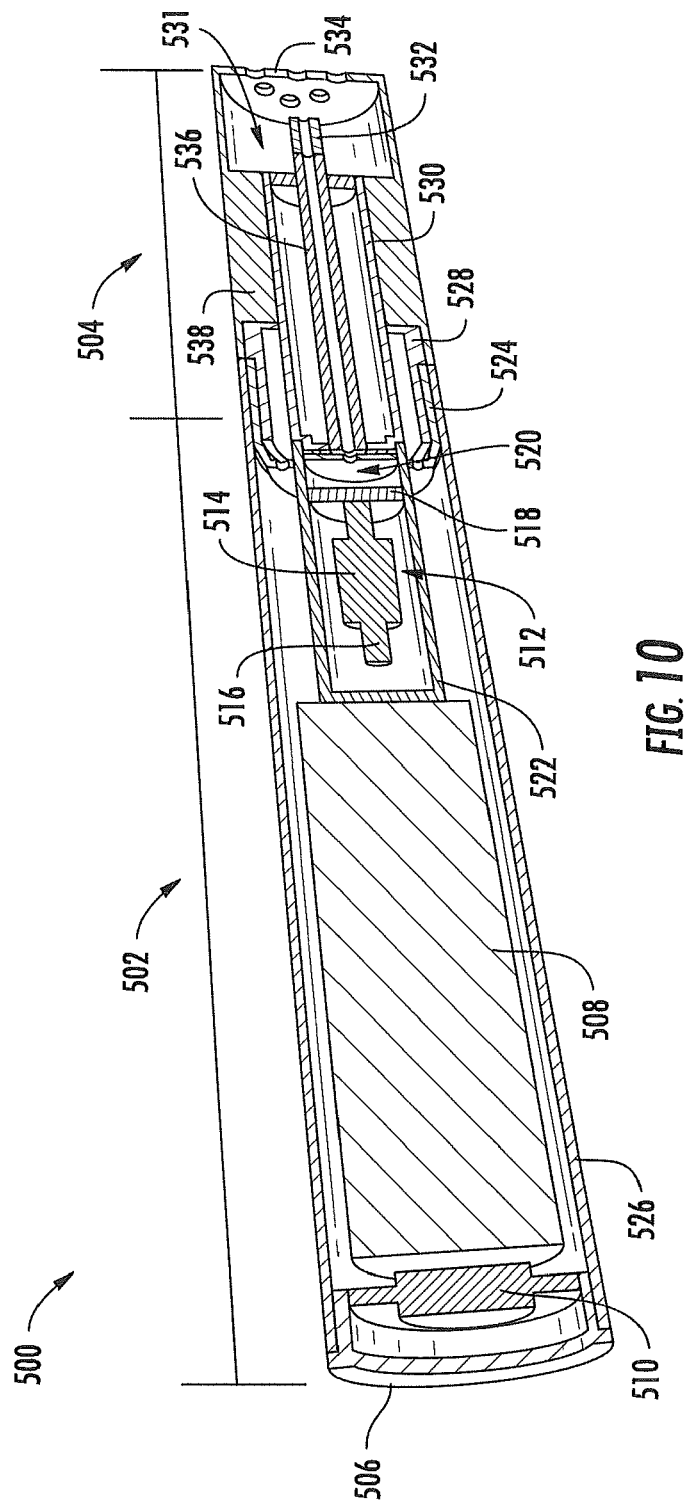
Figure 11:
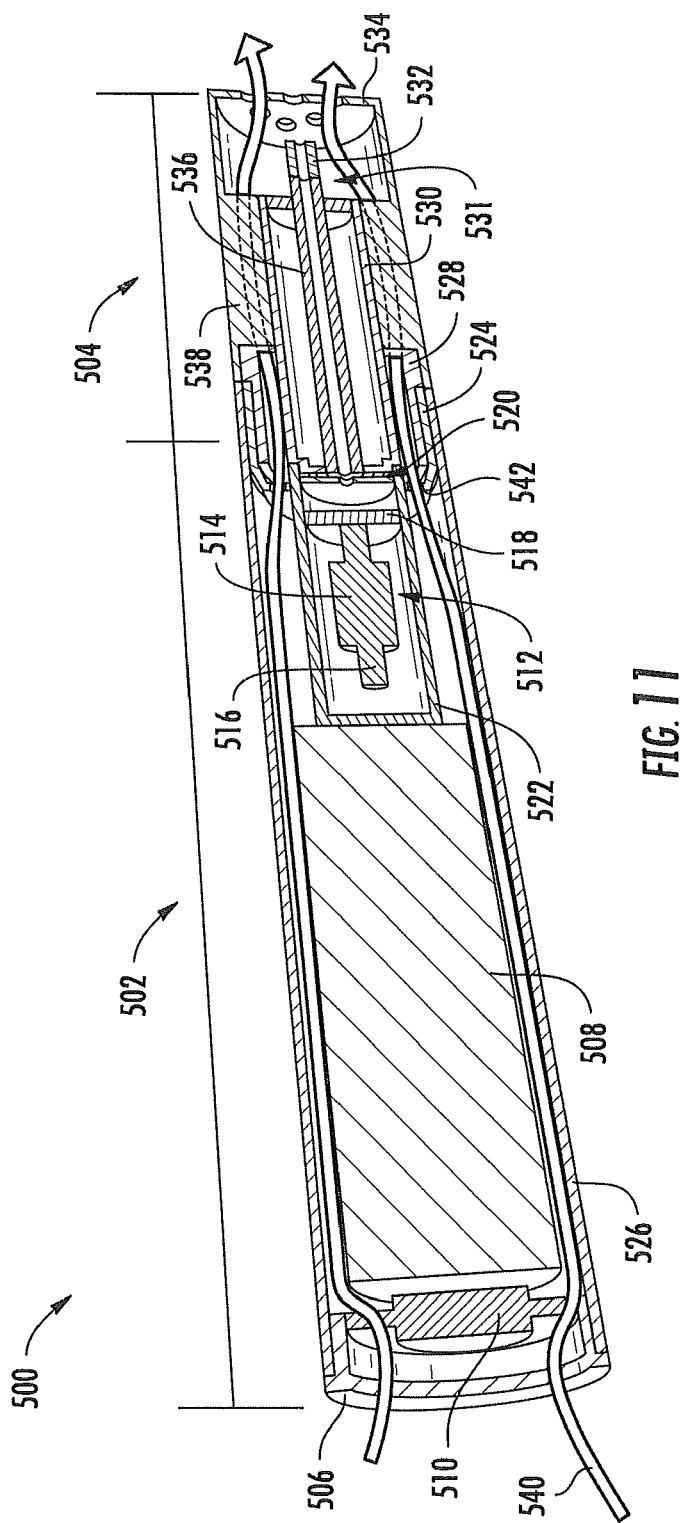
Figure 12:
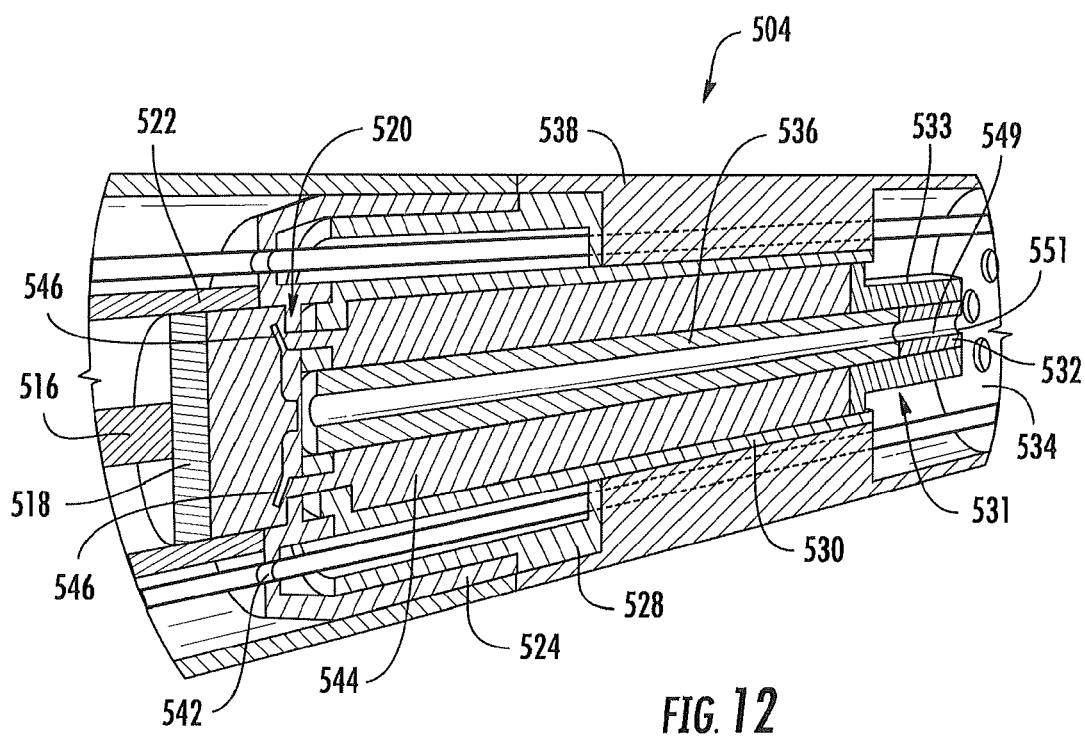
Figure 13:
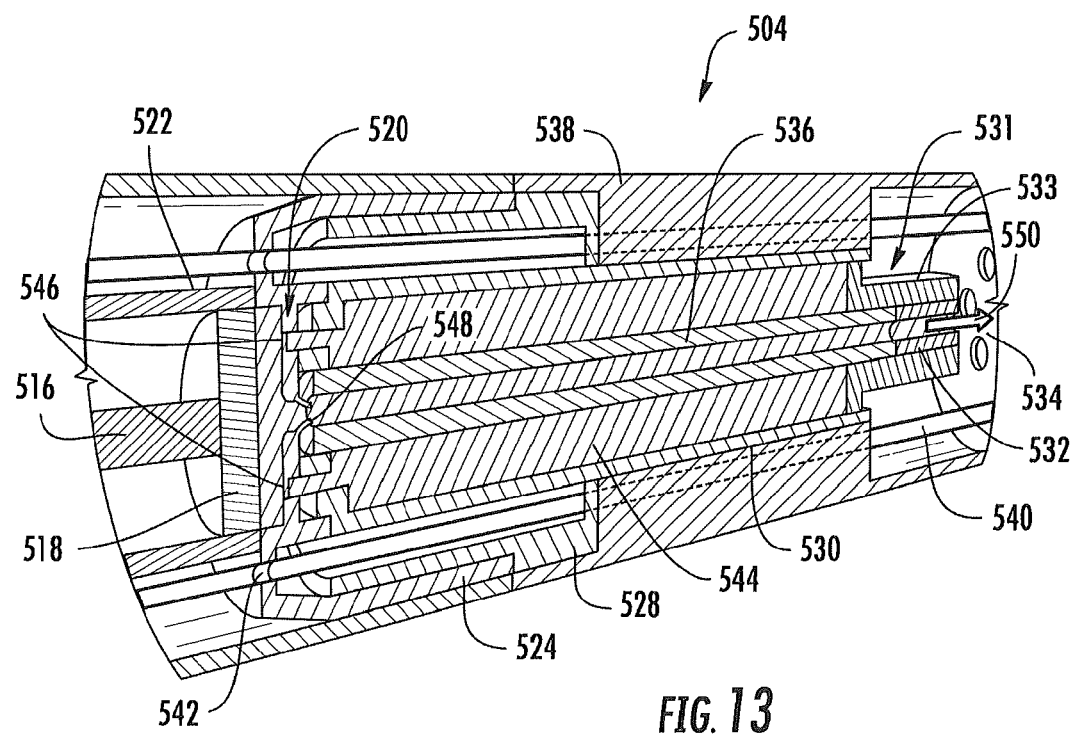
Figure 14:
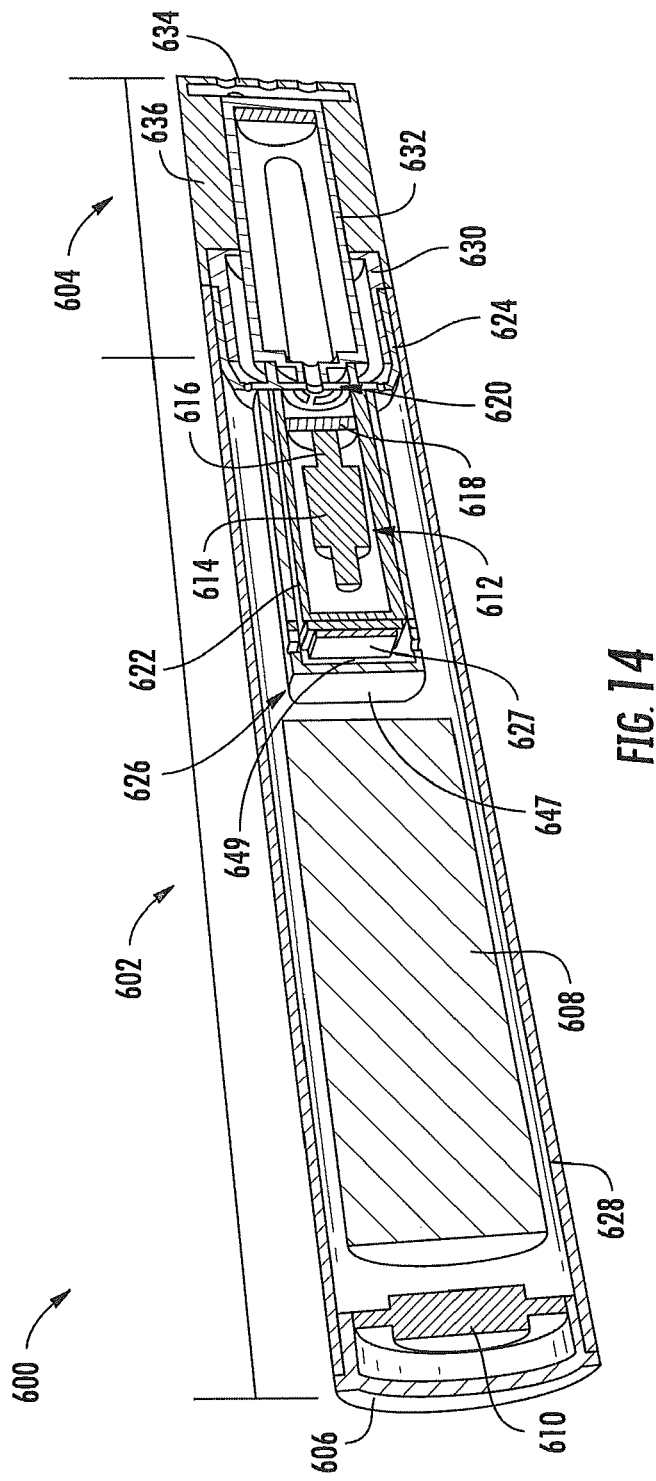
Figure 15:
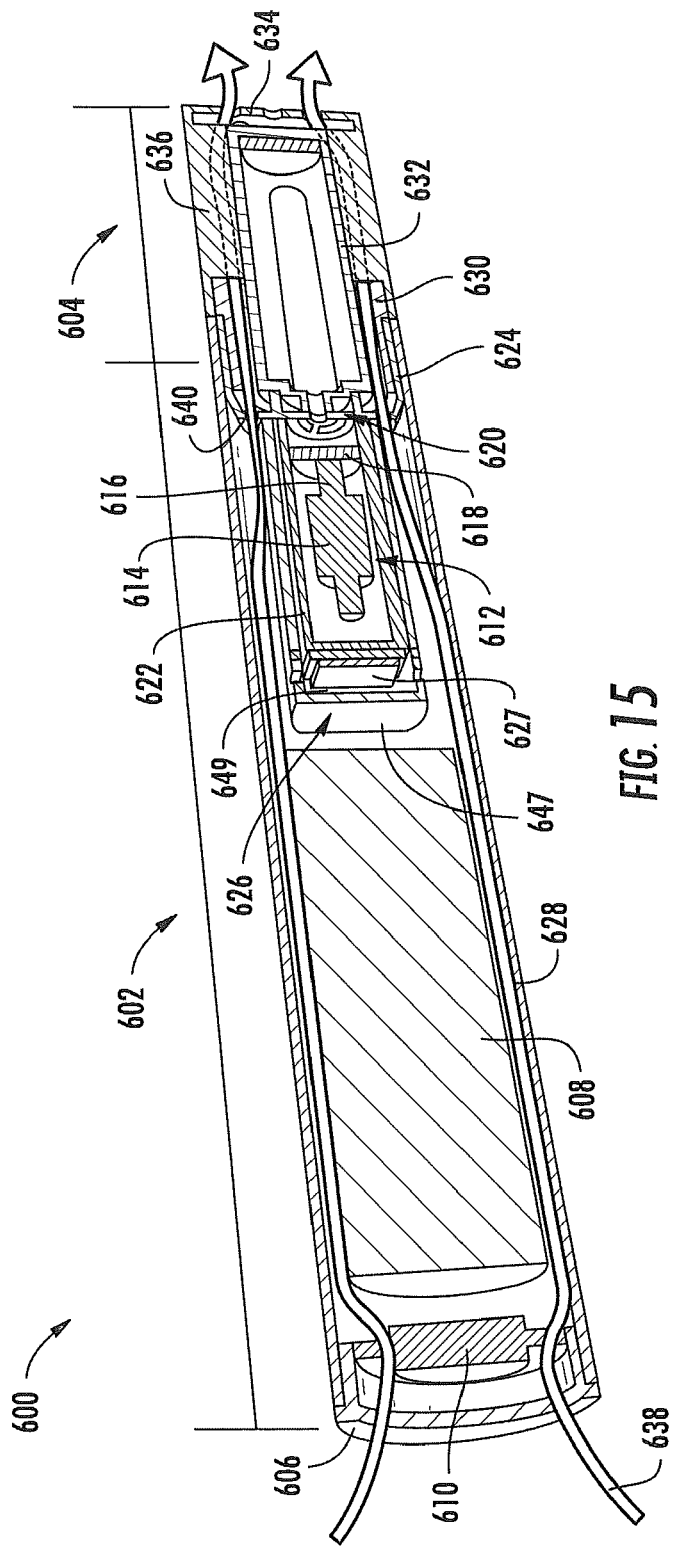
Figure 16:
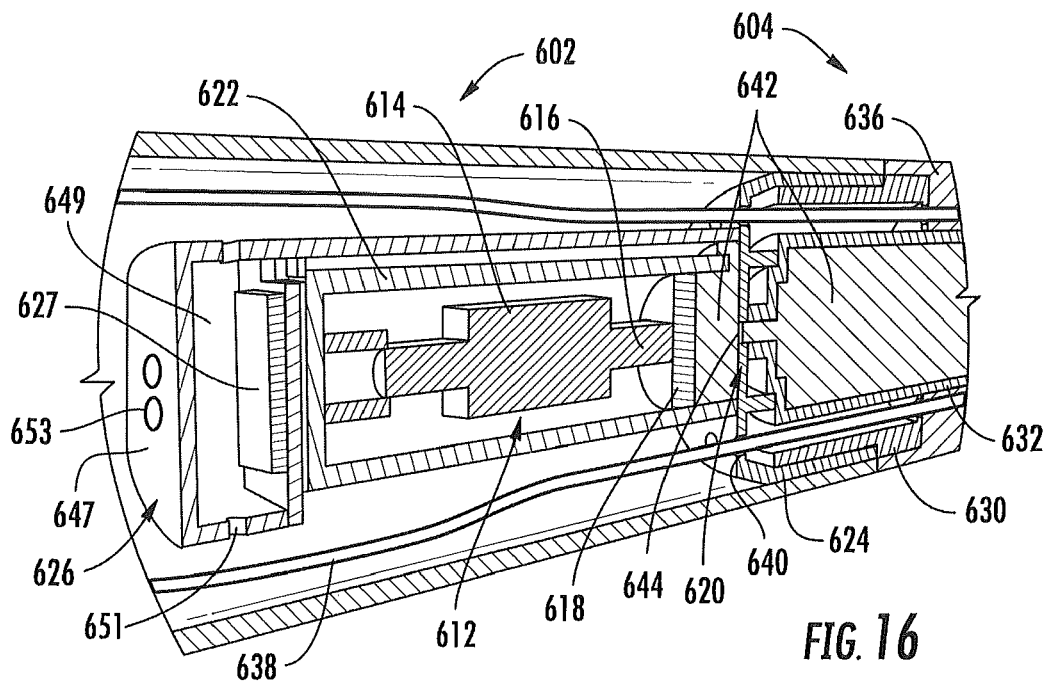
Figure 17:
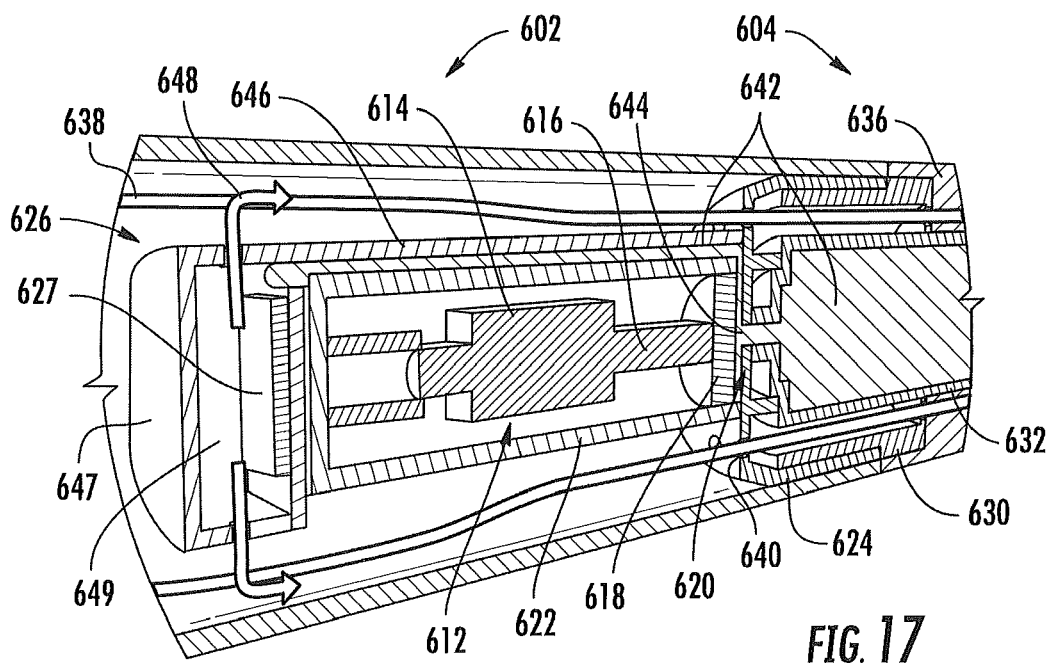
Figure 18:
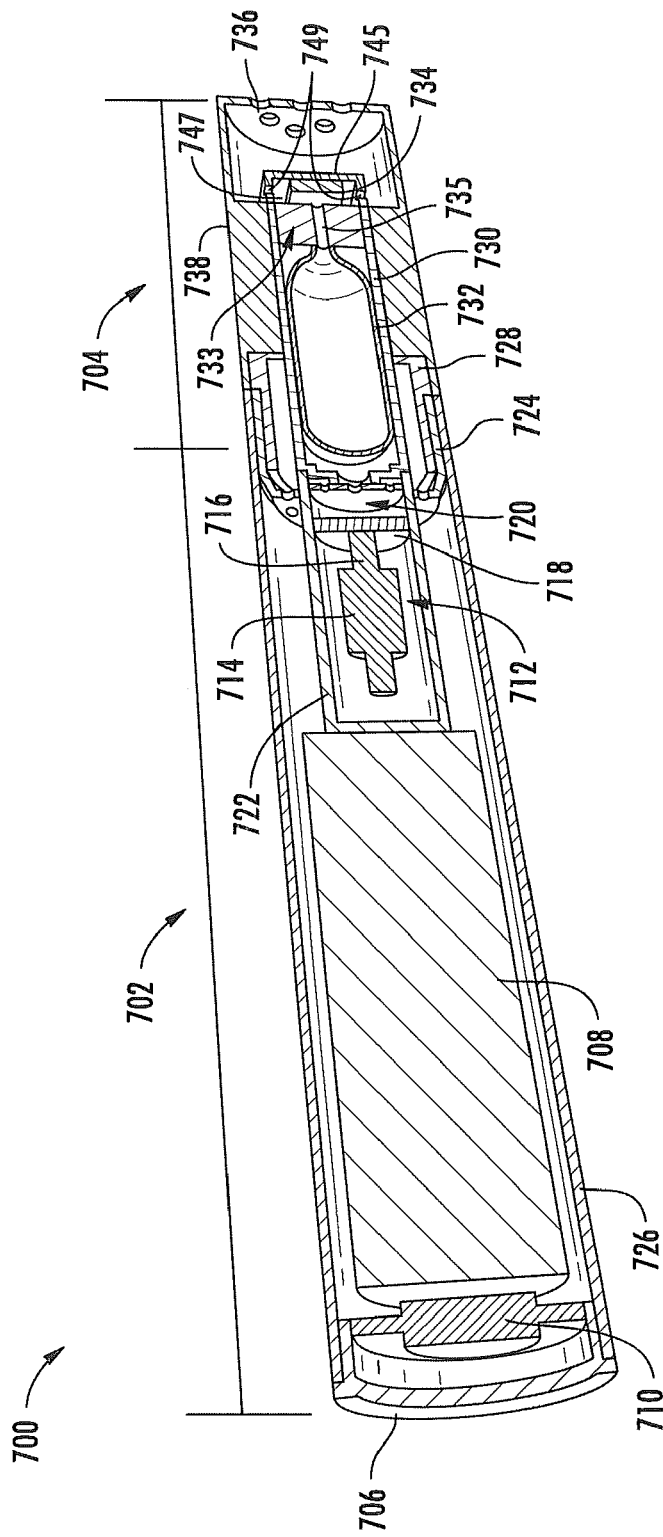
Figure 19:
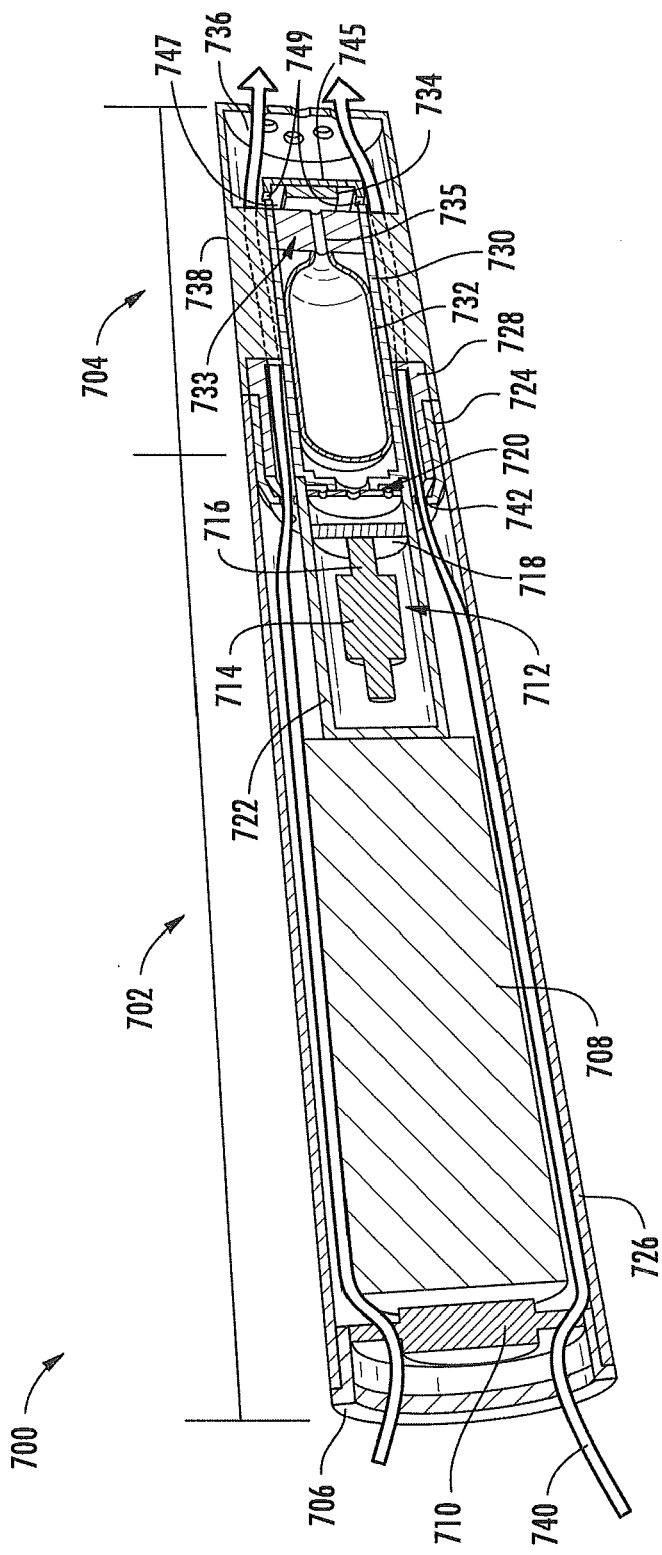
Figure 20:
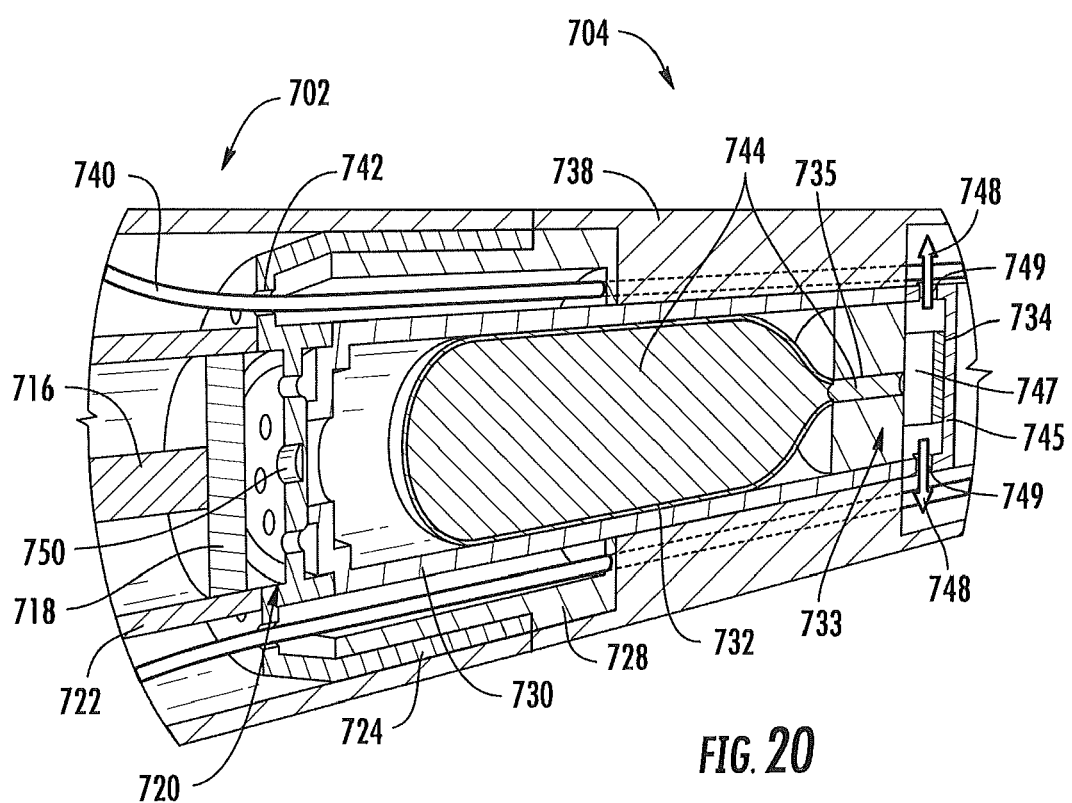
Figure 21:
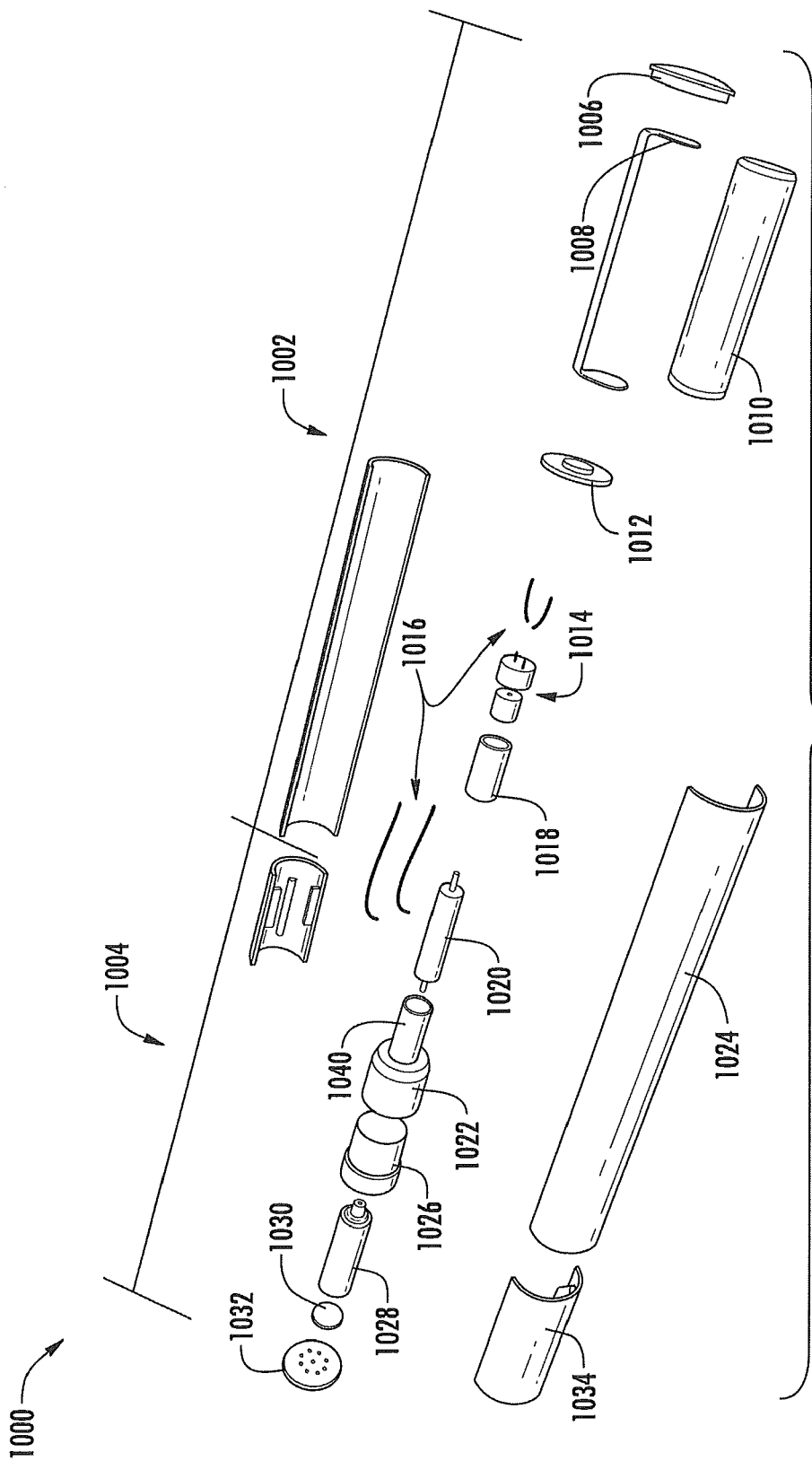
Figure 22:
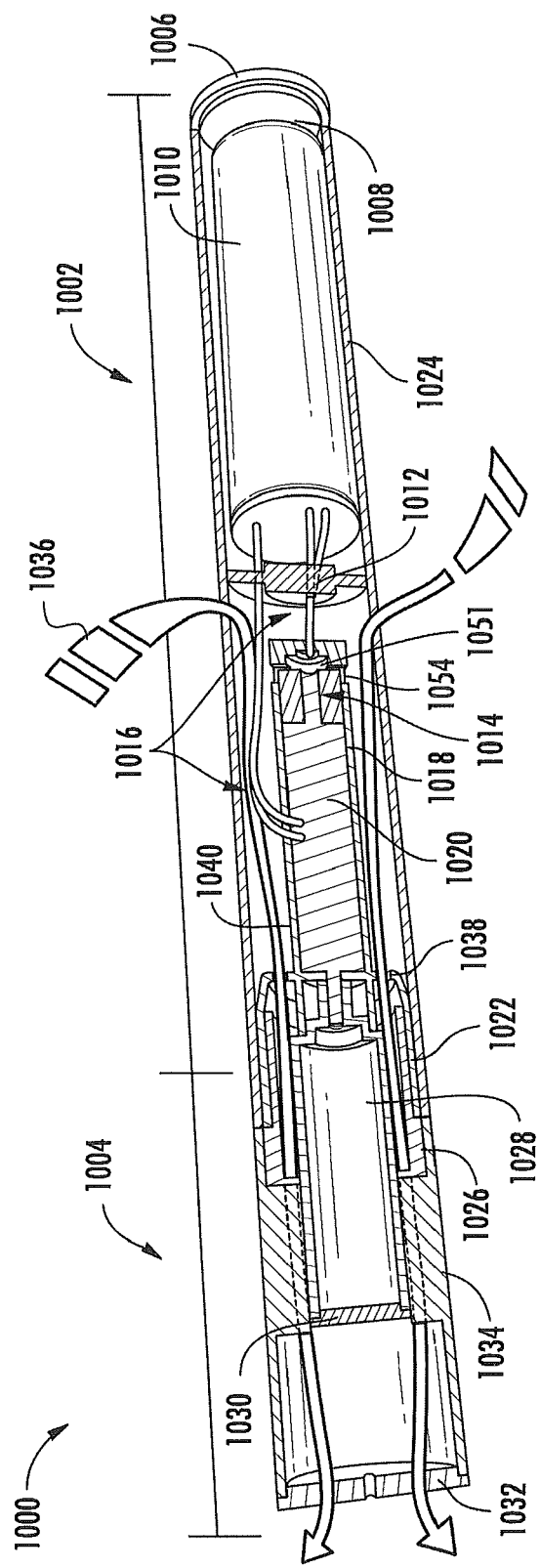
Figure 23:
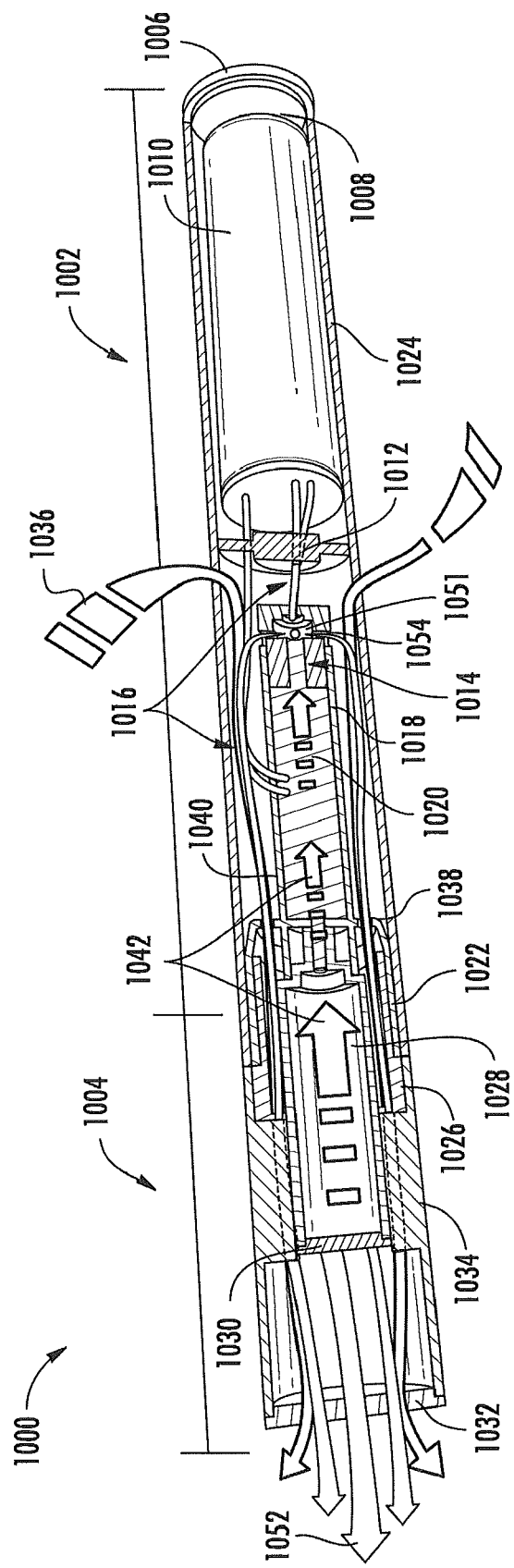
Figure 24:
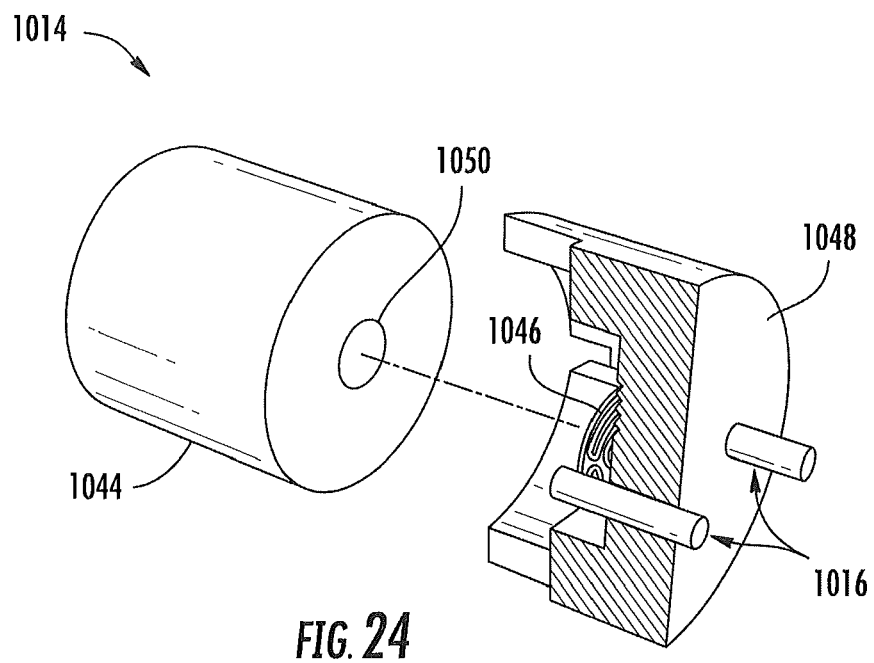
Figure 25:
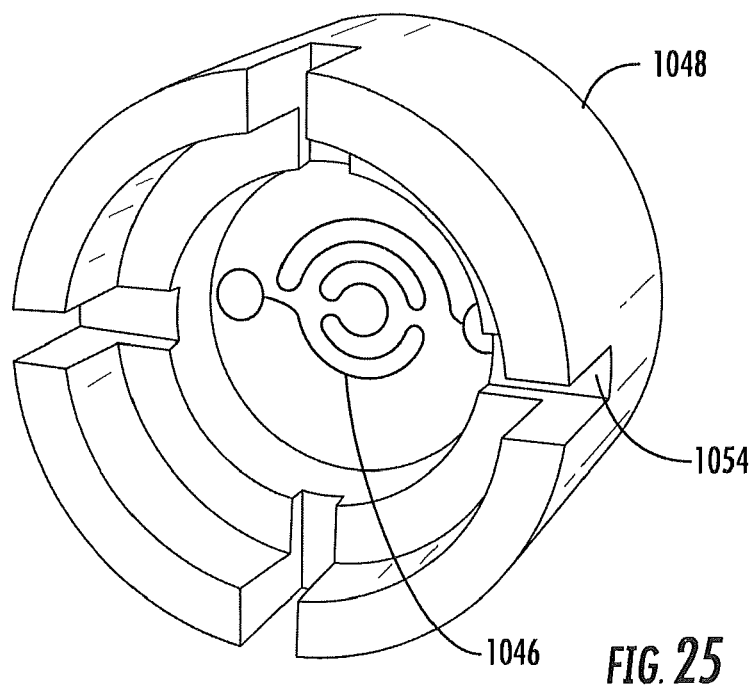
Figure 26:
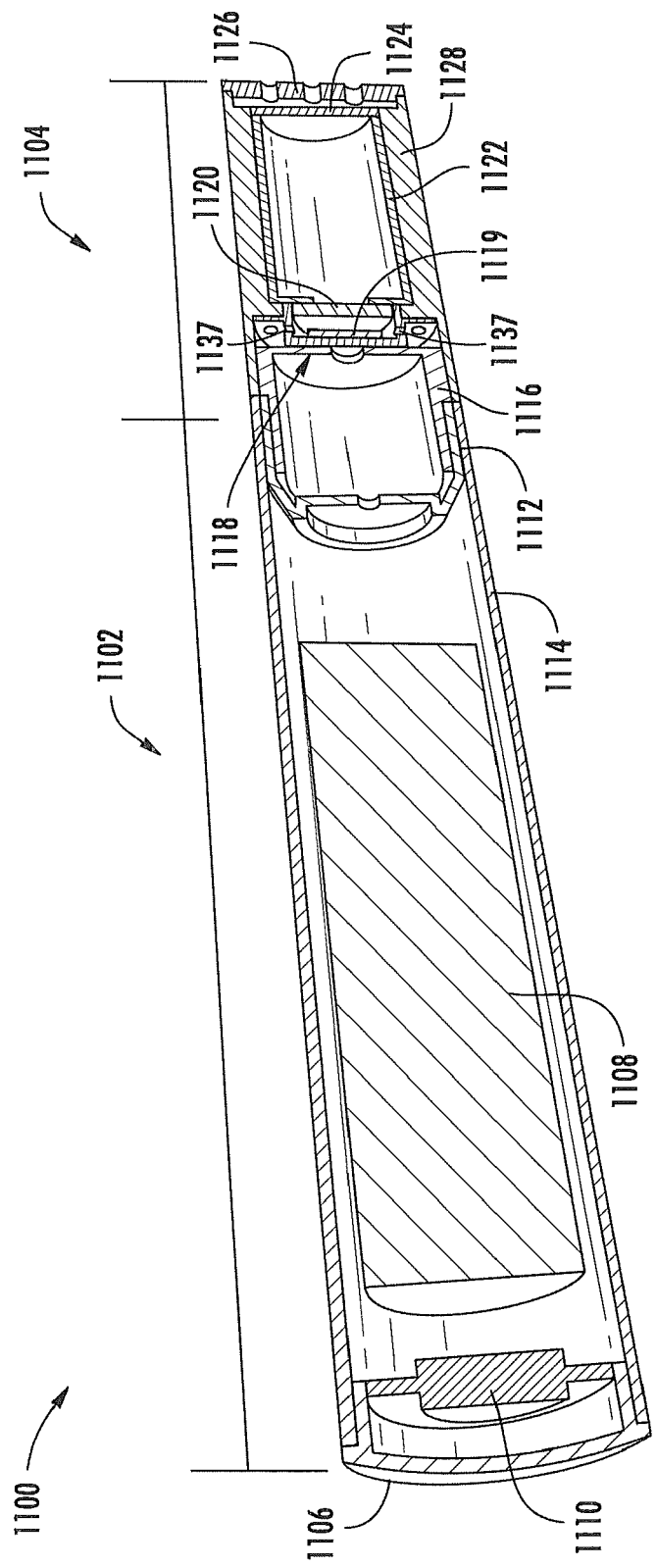
Figure 27:
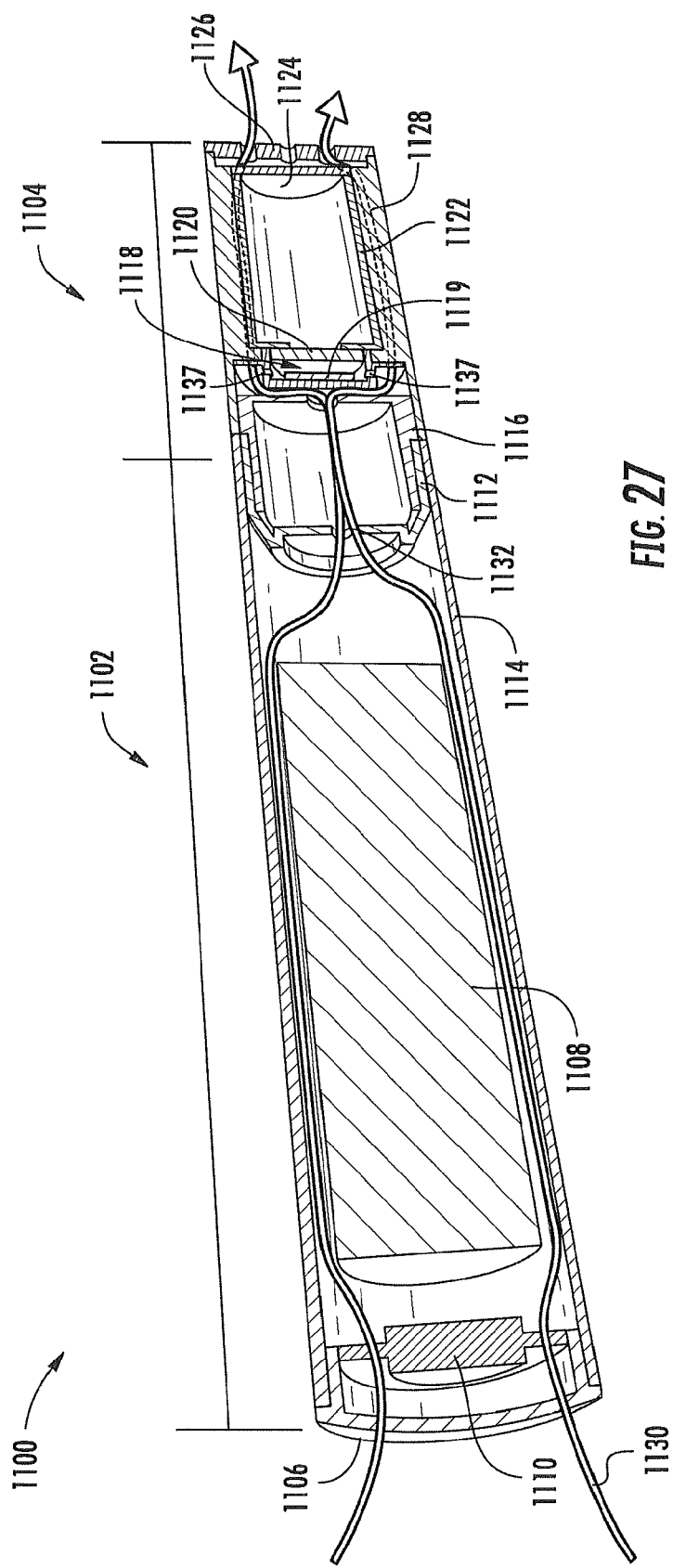

Having thus described the disclosure in the foregoing general terms, reference will now be made to the accompanying drawings, which are not necessarily drawn to scale, and wherein:

FIG. 1 illustrates an exploded view of a control body according to an example embodiment of the present disclosure;

FIG. 2 illustrates an exploded view of an aerosol delivery device including a pump powered by a linear motor and configured to deliver an aerosol precursor composition to an atomizer on a same side thereof as a reservoir according to an example embodiment of the present disclosure;

FIG. 3 illustrates a modified sectional view through the aerosol delivery device of FIG. 2 showing airflow therethrough according to an example embodiment of the present disclosure;

FIG. 4 illustrates an enlarged exploded view of the linear motor of the aerosol delivery device of FIG. 2 according to an example embodiment of the present disclosure;

FIG. 5 illustrates a modified sectional view through the aerosol delivery device of FIG. 2 showing operation of the pump according to an example embodiment of the present disclosure;

FIG. 6 illustrates an enlarged exploded perspective view of an atomizer of the aerosol delivery device of FIG. 2 according to an example embodiment of the present disclosure;

FIG. 7 illustrates an opposing enlarged exploded perspective view of an atomizer of the aerosol delivery device of FIG. 2 according to an example embodiment of the present disclosure;

FIG. 8 illustrates a modified sectional view through the reservoir of the aerosol delivery device of FIG. 2;

FIG. 9 illustrates a modified sectional view through the aerosol delivery device of FIG. 2 during production of vapor;

FIG. 10 illustrates a sectional view through an aerosol delivery device including a pump powered by a linear motor and configured to deliver an aerosol precursor composition to an atomizer on a same side thereof as a reservoir according to an example embodiment of the present disclosure;

FIG. 11 illustrates a sectional view through the aerosol delivery device of FIG. 10 showing airflow therethrough according to an example embodiment of the present disclosure;

FIG. 12 illustrates an enlarged sectional view of the aerosol delivery device of FIG. 10 showing the pump drawing the aerosol precursor composition out of the reservoir according to an example embodiment of the present disclosure;

FIG. 13 illustrates an enlarged sectional view of the aerosol delivery device of FIG. 10 showing the pump pumping the aerosol precursor composition to the atomizer according to an example embodiment of the present disclosure;

FIG. 14 illustrates a section view through an aerosol delivery device including a pump powered by a linear motor and configured to deliver an aerosol precursor composition to an atomizer on an opposing side thereof as compared to a reservoir according to an example embodiment of the present disclosure;

FIG. 15 illustrates a sectional view through the aerosol delivery device of FIG. 14 showing airflow therethrough according to an example embodiment of the present disclosure;

FIG. 16 illustrates an enlarged sectional view through the aerosol delivery device of FIG. 14 showing the pump drawing the aerosol precursor composition out of the reservoir according to an example embodiment of the present disclosure;

FIG. 17 illustrates an enlarged sectional view through the aerosol delivery device of FIG. 14 showing the pump pumping the aerosol precursor composition to the atomizer according to an example embodiment of the present disclosure;

FIG. 18 illustrates a sectional view through an aerosol delivery device including a pump configured to dispense an aerosol precursor composition from a bag according to an example embodiment of the present disclosure;

FIG. 19 illustrates an enlarged sectional view through the aerosol delivery device of FIG. 18 showing airflow therethrough according to an example embodiment of the present disclosure;

FIG. 20 illustrates an enlarged sectional view through the aerosol delivery device of FIG. 18 showing the pump pumping the aerosol precursor composition from the bag to an atomizer according to an example embodiment of the present disclosure;

FIG. 21 illustrates an exploded view of an aerosol delivery device including a pump configured for insertion of an end thereof into a reservoir according to an example embodiment of the present disclosure;

FIG. 22 illustrates a modified sectional view through the aerosol delivery device of FIG. 21 showing airflow therethrough according to an example embodiment of the present disclosure;

FIG. 23 illustrates a sectional view through the aerosol delivery device of FIG. 21 showing production of vapor according to an example embodiment of the present disclosure;

FIG. 24 illustrates an enlarged modified exploded view of an atomizer of the aerosol delivery device of FIG. 21 according to an example embodiment of the present disclosure;

FIG. 25 illustrates an opposing enlarged partial perspective view of the atomizer of the aerosol delivery device of FIG. 21 according to an example embodiment of the present disclosure;

FIG. 26 illustrates a sectional view through an aerosol delivery device including a micropump according to an example embodiment of the present disclosure;

FIG. 27 illustrates a sectional view through the aerosol delivery device of FIG. 26 showing airflow therethrough according to an example embodiment of the present disclosure;

FIG. 28 illustrates an enlarged sectional view through the aerosol delivery device of FIG. 26 showing the micropump dispensing an aerosol precursor composition to an atomizer according to an example embodiment of the present disclosure; and FIG. 29 schematically illustrates a method for aerosolization with an aerosol delivery device including dispensing an aerosol precursor composition with a positive displacement apparatus.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

As described hereinafter, embodiments of the present disclosure relate to aerosol delivery systems, devices, and components therefor. Aerosol delivery systems according to the present disclosure use electrical energy to heat a material (preferably without combustion the material to any significant degree) to form an incapable substance; and components of such systems have the form of articles that are most preferably sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In preferred embodiments, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being suitable vapor-producing articles or medicament delivery articles. Thus, such articles or devices can be adapted so as to provide one or more substances (e.g., flavors and/or pharmaceutical active ingredients) in an incapable form or state. For example, incapable substances can be substantially in the form of a vapor (i.e., a substance that is in the gas phase at a temperature lower than its critical point). Alternatively, incapable substances can be in the form of an aerosol (i.e., a suspension of fine solid particles or liquid droplets in a gas).

Aerosol delivery systems of the present disclosure most preferably comprise some combination of a power source (i.e, an electrical power source), at least one control component (e.g., means for actuating, controlling, regulating and/or ceasing power supplied for heat generation, such as by controlling electrical current flow from an electrical power release unit to other components of the aerosol generating piece), a heater or heat generation component (e.g., an electrical resistance heating element and related components commonly referred to as providing an "atomizer"), and an aerosol precursor (e.g., a composition that commonly is a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the aerosol generation piece such that aerosol generated can be withdrawn therefrom upon draw). Exemplary formulations for aerosol precursor materials that may be used according to the present disclosure are described in U.S. Pat. Pub. No. 2013/0008457 to Zheng et al., the disclosure of which is incorporated herein by reference in its entirety. More specific formats, configurations and arrangements of components within the aerosol delivery systems of the present disclosure will be evident in light of the further disclosure provided hereinafter.

Alignment of the components within the aerosol delivery device can vary. In specific embodiments, the aerosol precursor composition can be located near an end of the article (e.g., within a cartridge, which in certain circumstances can be replaceable and disposable), which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor composition (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an incapable substance is released in the form of a vapor or aerosol or mixture thereof. Additionally, the selection of various aerosol delivery device components can be appreciated upon consideration of the commercially available electronic aerosol delivery devices, such as those representative products listed in the background art section of the present disclosure.

An aerosol delivery device incorporates a battery or other electrical power source to provide current flow sufficient to provide various functionalities to the article, such as powering of a heater, powering of control systems, powering of indicators, and the like. The power source can take on various embodiments. Preferably, the power source is able to deliver sufficient power to rapidly heat the heating element to provide for aerosol formation and power the article through use for the desired duration of time. The power source preferably is sized to fit conveniently within the aerosol delivery device so that the aerosol delivery device can be easily handled; and additionally, a preferred power source is of a sufficiently light weight to not detract from a desirable smoking experience.

An aerosol delivery device can include a cartridge and a control body that can be permanently or detachably aligned in a functioning relationship. Various embodiments of engagement between the cartridge and the control body may be employed such as a threaded engagement, a press-fit engagement, an interference fit, a magnetic engagement, or the like. The aerosol delivery device may be substantially rod-like, substantially tubular shaped, or substantially cylindrically shaped in some embodiments when the cartridge and the control body are in an assembled configuration. However, various other shapes and configurations may be employed in other embodiments.

In specific embodiments, one or both of the cartridge and the control body may be referred to as being disposable or as being reusable. For example, the control body may have a replaceable battery or a rechargeable battery and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge may comprise a single-use cartridge, as disclosed in U.S. Pat. Pub. No. 2014/0060555 to Chang et al., which is incorporated herein by reference in its entirety.

In some embodiments a cartridge may include a base that may comprise anti-rotation features that substantially prevent relative rotation between the cartridge and the control body as disclosed in U.S. patent application Ser. No. 13/840, 264 to Novak et al., filed Mar. 15, 2013, which is incorporated herein by reference in its entirety.

An aerosol delivery device may include a component configured to hold an aerosol precursor composition. The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robin son et al., which is incorporated herein by reference in its entirety. Additional representative types of aerosol precursor compositions are set forth in U.S. Pat. No. 4,793, 365 to Sensabaugh, Jr. Et al.; U.S. Pat. No. 5,101,839 to Jakob et al.; PCT WO 98/57556 to Biggs et al.; U.S. patent application Ser. No. 14/245,105 to Henry, Jr., filed Apr. 4, 2014; and Chemical and Biological Studies on New Cigarette Prototypes that Heat Instead of Burn Tobacco, R. J. Reynolds Tobacco Company Monograph (1988); the disclosures of which are incorporated herein by reference in their entireties.

A variety of heater components may be used in the present aerosol delivery device. In various embodiments, one or more microheaters or like solid state heaters may be used. Embodiments of microheaters that may be utilized are further described herein. Further microheaters and atomizers incorporating microheaters suitable for use in the presently disclosed devices are described in U.S. Pat. Pub. No. 2014/ 0060554 to Collett et al., which is incorporated herein by reference in its entirety. In some embodiments a heating element may be formed by winding a wire about a liquid transport element as described in U.S. patent application Ser. No. 13/708,381 to Ward et al., filed Dec. 7, 2012, which is incorporated herein by reference in its entirety. Further, in some embodiments the wire may define a variable coil spacing, as described in U.S. patent application Ser. No. 13/827,994 to DePiano et al., filed Mar. 14, 2013, which is incorporated herein by reference in its entirety. Various embodiments of materials configured to produce heat when electrical current is applied therethrough may be employed to form a resistive heating element. Example materials from which the wire coil may be formed include Kanthal (Fe-CrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic). In further embodiments a stamped heating element may be employed in the atomizer, as described in U.S. patent application Ser. No. 13/842,125 to DePiano et al., filed Mar. 15, 2013, which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. Pub. No. 2014/0060554 to Collett et al., which is incorporated herein by reference, as noted above.

In some embodiments the aerosol delivery devices of the present disclosure may include a control body and a cartridge. When the control body is coupled to the cartridge, an electronic control component in the cartridge may form an electrical connection with the control body. The control body may thus employ the electronic control component to determine whether the cartridge is genuine and/or perform other functions. Further, various examples of electronic control components and functions performed thereby are described in U.S. Pat. App. Pub. No. 2014/0096781 to Sears et al., which is incorporated herein by reference in its entirety.

During use, a user may draw on a mouthpiece of the cartridge of the aerosol delivery device. This may pull air through an opening in the control body or in the cartridge. For example, in one embodiment an opening may be defined between the coupler and the outer body of the control body, as described in U.S. patent application Ser. No. 13/841,233 to DePiano et al., filed Mar. 15, 2013, which is incorporated herein by reference in its entirety. However, the flow of air may be received through other parts of the aerosol delivery device in other embodiments.

A sensor in the aerosol delivery device (e.g., a puff or flow sensor in the control body) may sense the puff. When the puff is sensed, the control body may direct current to the heater through a circuit. Accordingly, the heater may vaporize the aerosol precursor composition, and the mouthpiece may allow passage of air and entrained vapor (i.e., the components of the aerosol precursor composition in an incapable form) from the cartridge to a consumer drawing thereon.

Various other details with respect to the components that may be included in the cartridge, are provided, for example, in U.S. patent application Ser. No. 13/840,264 to Novak et al., filed Mar. 15, 2013, which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heater terminals of an atomizer in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow tube, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 11 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 3 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 4 thereof illustrates a perspective view of a base with an anti-rotation mechanism; FIG. 5 thereof illustrates a perspective view of a coupler with an anti-rotation mechanism; and FIG. 6 thereof illustrates a sectional view through the base of FIG. 4 thereof and the coupler of FIG. 5 thereof in an engaged configuration.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. Pub. No. 2014/0000638 to Sebastian et al., which is incorporated herein by reference in its entirety.

FIG. 1 illustrates an exploded view of a control body 300 of an aerosol delivery device according to an example embodiment of the present disclosure. As illustrated, the control body 300 may comprise a coupler 302, an outer body 304, a sealing member 306, an adhesive member 308 (e.g., KAPTON® tape), a flow sensor 310 (e.g., a puff sensor or pressure switch), a control component 312, a spacer 314, an electrical power source 316 (e.g., a battery, which may be rechargeable), a circuit board with an indicator 318 (e.g., a light emitting diode (LED)), a connector circuit 320, and an end cap 322. Examples of electrical power sources are described in U.S. Pat. App. Pub. No. 2010/0028766 by Peckerar et al., the disclosure of which is incorporated herein by reference in its entirety. An exemplary mechanism that can provide puff-actuation capability includes a Model 163PC01D36 silicon sensor, manufactured by the Micro-Switch division of Honeywell, Inc., Freeport, Ill. Further examples of demand-operated electrical switches that may be employed in a heating circuit according to the present disclosure are described in U.S. Pat. No. 4,735,217 to Gerth et al., which is incorporated herein by reference in its entirety. Further description of current regulating circuits and other control components, including microcontrollers that can be useful in the present aerosol delivery device, are provided in U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., and U.S. Pat. No. 7,040,314 to Nguyen et al., all of which are incorporated herein by reference in their entireties. Reference also is made to the control schemes described in U.S. application Ser. No. 13/837,542 to Ampolini et al., filed Mar. 15, 2013, which is incorporated herein by reference in its entirety.

In one embodiment the indicator 318 may comprise one or more light emitting diodes. The indicator 318 can be in communication with the control component 312 through the connector circuit 320 and illuminate, for example, during a user drawing on a cartridge coupled to the coupler 302, as detected by the flow sensor 310. The end cap 322 may be adapted to make visible the illumination provided thereunder by the indicator 318. Accordingly, the indicator 318 may illuminate during use of the aerosol delivery device to simulate the lit end of a smoking article. However, in other embodiments the indicator 318 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. App. Pub. Nos. 2006/0196518 and 2009/0188490 to Hon; U.S. Pat. App. Pub. No. 2009/0272379 to Thorens et al.; U.S. Pat. App. Pub. Nos. 2009/0260641 and 2009/0260642 to Monsees et al.; U.S. Pat. App. Pub. Nos. 2008/0149118 and 2010/0024834 to Oglesby et al.; U.S. Pat. App. Pub. No. 2010/0307518 to Wang; WO 2010/091593 to Hon; WO 2013/089551 to Foo; and U.S. patent application Ser. No. 13/841,233 to DePiano et al., filed Mar. 15, 2013, each of which is incorporated herein by reference in its entirety. A variety of the materials disclosed by the foregoing documents may be incorporated into the present devices in various embodiments, and all of the foregoing disclosures are incorporated herein by reference in their entireties.

Accordingly, example embodiments of aerosol delivery devices are described above. However, the present disclosure provides various other embodiments of aerosol delivery devices. As described hereinafter, such aerosol delivery devices may include differing configurations of components for storing, delivering, and/or vaporizing an aerosol precursor composition.

In this regard, FIG. 2 illustrates an exploded view of an aerosol delivery device 400 according to an example embodiment of the present disclosure. As illustrated, the aerosol delivery device 400 may include a control body 402 and a cartridge 404. The control body 402 may include an indicator 406 (e.g., an LED), a circuit board 408, an electrical power source 410 (e.g., a battery, which may be rechargeable), a flow sensor 412, a motor assembly 414, wiring 416, a coupler 418, and an outer body 420. The cartridge 404 may include a base 422, a piston 424, a reservoir 426, an atomizer 428, a mouthpiece 430, and an outer body 432. The base 422 of the cartridge 404 may be configured to releasably engage the coupler 418 of the control body 402 to form a mechanical and electrical connection therebetween.

FIG. 3 illustrates a modified sectional view through the aerosol delivery device 400 as assembled. More particularly, FIG. 3 illustrates a flow path of air through the aerosol delivery device when a user draws on the mouthpiece 430. As illustrated, an airflow or flow of ambient air 434 may enter the aerosol delivery device 400 and travel past the flow sensor 412. Note that in embodiments disclosed herein, the flow sensor may comprise a pressure sensor such that the air need not directly contact the sensor for a puff to be detected. The air 434 may then travel through the coupler 418 through one or more apertures 436 (see, FIG. 4), through the base 422, around the reservoir 426 and the atomizer 428, and out the mouthpiece 430.

As illustrated in FIG. 3, in one embodiment the air 434 may enter the aerosol delivery device 400 through the outer body 420 (e.g., through one or more apertures defined therein). However, in other embodiments the air may enter the aerosol delivery device at an alternate location. For example, the air may enter through a longitudinal end of the aerosol delivery device opposite from the mouthpiece, though the coupler or the base, or at a location between the base and the mouthpiece. Accordingly, it should be understood that the particular airflow patterns described herein are provided for example purposes only.

When the flow sensor 412 detects the puff, the motor assembly 414 may be actuated. In this regard, FIG. 4 illustrates an enlarged, exploded, partial view of the motor assembly 414 and the coupler 418. As illustrated, the motor assembly 414 may include an actuator 438 and a rod 440. As further illustrated in FIG. 4, the coupler 418 may include a receptacle 442 configured to receive and hold the actuator 438 of the motor assembly 414 in place. The actuator 438 may be configured to linearly displace the rod 440. Accordingly, the motor assembly 414 may comprise a linear motor in some embodiments. By way of further example, in one embodiment the motor assembly 414 may comprise a SQUIGGLE motor as sold by New Scale Technologies, Inc. of Victor, N.Y. Such a motor may produce both linear and rotary movement of the rod 440.

As illustrated in FIG. 5, when the motor assembly 414 is actuated, the actuator 438 may linearly displace the rod 440 into the cartridge 404 such that the piston 424 presses against an aerosol precursor composition 444 in the reservoir 426. In this regard, the reservoir 426 may define a pump housing and the actuator 438 may be configured to displace the piston 424 within the pump housing to dispense the aerosol precursor composition 426 therefrom. Accordingly, the aerosol precursor composition may be directed to the atomizer 428.

FIG. 6 illustrates an enlarged partial perspective view of the atomizer 428. As illustrated, the atomizer 428 may include a fluid delivery tube 446, a heater disk 448, a cap 450, a heating element 452, and first and second terminals 454a,b. The heating element 452 and/or the first and second terminals 454a,b may comprise a printed circuit in some embodiments. In this regard, the heating element 452 may be coupled to, imbedded in, or printed on the heater disk 448 in some embodiments. Similarly, the first and second terminals 454a,b may be coupled to, imbedded in, or printed on the heater disk 448 in some embodiments.

FIG. 7 illustrates an opposing enlarged partial perspective view of the atomizer 428 and the reservoir 426. As illustrated in FIGS. 7 and 8, the fluid delivery tube 446 may include an aperture 456 extending from the reservoir 426 toward the heating element 452. The aperture 456 may connect to a groove 458 defined in the fluid delivery tube 446 at an end thereof. As illustrated, a size, shape, and/or pattern of the heating element 452 may at least partially match that of the groove 458. In one embodiment the fluid delivery tube 446 and the cap 450 may cooperatively define a chamber 461 (see, e.g., FIG. 3) in which the heating element 452 is positioned and to which the aerosol precursor composition 444 is delivered. Thus, issues with respect to the aerosol precursor composition 444 being directed into the air 434 and to a user without being vaporized may be avoided. In this regard, the aerosol precursor composition 444 may be directed into contact with the heating element 452 at the chamber 461 to ensure vaporization thereof.

In this regard, when the flow sensor 412 detects a puff on the aerosol delivery device 400, current from the electrical power source 410 may be directed through the terminals 454a,b to cause the heating element 452 to produce heat. Accordingly, the aerosol precursor composition directed through the aperture 456 and into the groove 458 may be heated and vaporized by the heating element 452 in the groove. The aerosol precursor composition 444 may be retained in the groove by the heater disk 448 and/or the heating element 452. Thereby, the aerosol precursor composition 444 and vapor produced by the heating element 452 may be forced to follow a path defined by the groove 458 which terminates at a round groove 462. The resultant vapor 460 may then exit the chamber 461 of the atomizer 428 through the round groove 462 and radially extending grooves 464 defined in the fluid delivery tube 446 and overlapping grooves 466 in the reservoir 426 as illustrated in FIGS. 6-9.

The chamber 461 (see, e.g., FIG. 9) may be configured to provide for optimal rates of release of the vapor 460 therefrom and into the air 434. In this regard, the radially extending grooves 464 defined in the fluid delivery tube 446 and the overlapping grooves 466 in the reservoir 426 may be particularly sized and oriented so as to provide for a selected flow rate of the vapor from the chamber 461. Although grooves are described above as being employed to allow for outflow of vapor from the chamber, various other embodiments of outlet apertures such as one or more round holes may be employed in other embodiments.

Further, in one embodiment the housing may additionally define one or more inlet apertures in communication with the chamber. The inlet apertures may be configured to allow flow of air therethough into the chamber. Thus, as a user draws on the aerosol delivery device, air entering through the inlet apertures may mix with the vapor and exit through the outlet apertures (e.g., the grooves). In this regard, the inlet apertures may be positioned such that air flowing through the aerosol delivery device is incident upon the inlet apertures (e.g., the inlet apertures may extend substantially parallel to a longitudinal axis of the aerosol delivery device and hence substantially parallel to the airflow therethrough). Thus, the inlet apertures may assist in removing the vapor from the chamber. Baffles may additionally be positioned in and/or around the chamber in order to direct air into the chamber and/or direct the vapor out of the chamber.

Further, in some embodiments valves may be provided at one or both of the inlet apertures and the outlet apertures. Such valves may passively or actively open and close to allow flow of air into the chamber and/or allow flow of vapor out of the chamber. Alternatively or additionally, the inlet apertures and/or the outlet apertures may be particularly sized to provide a desired flow of the vapor from the chamber while ensuring substantially complete vaporization of the aerosol precursor composition.

FIG. 10 illustrates a sectional view through an aerosol delivery device 500 according to an additional example embodiment of the present disclosure. As illustrated, the aerosol delivery device 500 may include a control body 502 and a cartridge 504. The control body 502 may include an indicator 506 (e.g., an LED), an electrical power source 508 (e.g., a battery, which may be rechargeable), a flow sensor 510, a motor assembly 512 comprising an actuator 514 and a rod 516, a piston 518, a valve assembly 520, a pump housing 522, a coupler 524, and an outer body 526. The cartridge 504 may include a base 528, a reservoir 530, an atomizer 531 comprising a heating element 532 and a fluid delivery tube 536, a mouthpiece 534, and an outer body 538. The base 528 of the cartridge 504 may be configured to releasably engage the coupler 524 of the control body 502 to form a mechanical and electrical connection therebetween.

FIG. 11 illustrates an additional sectional view through the aerosol delivery device 500. More particularly, FIG. 11 illustrates a flow path of air through the aerosol delivery device 500 when a user draws on the mouthpiece 534. As illustrated, an airflow or flow of ambient air 540 may enter the aerosol delivery device 500 and travel past the flow sensor 510. Although the ambient air 540 is illustrated as flowing past the electrical power source 508, in other embodiments the air may not flow past the electrical power source and/or the flow sensor may be positioned at an alternative location. The air 540 may then travel through the coupler 524 through one or more apertures 542 defined therethrough, through the base 528, around the reservoir 530 and the atomizer 531, and out the mouthpiece 534.

As illustrated in FIG. 11, in one embodiment the air 540 may enter the aerosol delivery device 500 through a longitudinal end thereof, opposite from the mouthpiece 534. However, in other embodiments the air may enter the aerosol delivery device at an alternate location. For example, the air may enter through the coupler or the base, or at a location between the base and the mouthpiece. Accordingly, it should be understood that the particular airflow patterns described herein are provided for example purposes only.

When the flow sensor 510 detects the puff, the motor assembly 512 may be actuated. In this regard, FIG. 12 illustrates an enlarged partial sectional view through the aerosol delivery device 500. The actuator 514 may be configured to linearly displace the rod 516. Accordingly, the motor assembly 512 may comprise a linear motor in some embodiments. By way of further example, in one embodiment the motor assembly 512 may comprise a SQUIGGLE motor as sold by New Scale Technologies, Inc. of Victor, N.Y. Such a motor may produce both linear and rotary movement of the rod 516.

When the motor assembly 512 is actuated, the actuator 514 may linearly displace the rod 516 in a first direction (e.g., to the left in terms of the orientation illustrated in FIG. 12) such that the piston 518 retracts away from the cartridge 504 further into the pump housing 522. As illustrated in FIG. 12, this movement may draw an aerosol precursor composition 544 out of the reservoir 530, through one or more one-way valves 546 of the valve assembly 520, and into the pump housing 522.

Thereafter, the motor assembly 512 may be actuated such that the actuator 514 linearly displaces the rod 516 in a second direction (e.g., to the right in terms of the orientation illustrated in FIG. 12), opposite to the first direction, such that the piston 518 is directed toward the cartridge 504. Thereby, as illustrated in FIG. 13, the aerosol precursor composition 544 previously drawn into the pump housing 522 may be expelled through one or more second one-way valves 548 of the valve assembly 520. In this regard, whereas the first one-way valves 546 may only allow flow into the pump housing 522, the second one-way valves 548 may only allow flow out of the pump housing. Thus, the device may comprise at least two one-way valves opening in opposing directions to alternatively allow aerosol precursor composition out of the reservoir and into the atomizer.

Thus, as further illustrated in FIG. 13, the aerosol precursor composition 544 may be directed to the atomizer 531. In particular, the aerosol precursor composition 544 may be directed through the fluid delivery tube 536 to the heating element 532. As illustrated, in one embodiment the heating element 532 may define a tubular configuration whereby the aerosol precursor composition 544 may be directed therethrough and vaporized therein. In particular, the heating element 532 may be aligned with, or otherwise in fluid communication with, the fluid delivery tube 536 such that the aerosol precursor composition 544 directed through the fluid delivery tube is also directed through the heating element. In some embodiments, the atomizer 531 may comprise a fluid delivery tube 536 (which may be a capillary tube) that is adjacent to and co-linear with a substantially tubular heating element 532. Accordingly, by providing the heating element 532 with the tubular configuration, the atomizer 531 may define a chamber 549 (see, FIG. 12) to which the aerosol precursor composition 544 is delivered. Thus, issues with respect to the aerosol precursor composition 544 being directed into the air 540 and to a user without being vaporized may be avoided. In this regard, the aerosol precursor composition 544 may be directed into contact with the heating element 532 at the chamber 549 to ensure vaporization thereof. In some embodiments, a selectively permeable cover may be included at an outlet aperture 551 at or near the terminal end of the heating element 532 to allow exit of formed vapor 550 and substantially disallow exit of liquid aerosol precursor composition 544. Accordingly, leakage of any of the aerosol precursor composition which has not been vaporized may be avoided.

In this regard, when the flow sensor 510 detects a puff on the aerosol delivery device 500, current from the electrical power source 508 may be directed to the heating element 532 to produce heat. Accordingly, the aerosol precursor composition 544 directed thereto may be heated and vaporized to define an aerosol or vapor 550. The vapor 550 may then exit the chamber 549 through the outlet aperture 551, mix with the air 540, and exit through the mouthpiece 534.

The chamber 549 (see, e.g., FIG. 12) may be configured to provide for optimal rates of release of the vapor 550 therefrom and into the air 540. In this regard, the outlet aperture 551 may be particularly sized and oriented so as to provide for a selected flow rate of the vapor 550 from the chamber 549. Although the outlet aperture 551 is illustrated as defining a round configuration, various other embodiments of outlet apertures such as a plurality of apertures and/or non-circular apertures may be employed in other embodiments.

Further, in one embodiment the atomizer may additionally define one or more inlet apertures in communication with the chamber. The inlet apertures may be configured to allow flow of air therethough into the chamber. Thus, as a user draws on the aerosol delivery device, air entering through the inlet apertures may mix with the vapor and exit through the outlet aperture(s). In this regard, the inlet apertures may be positioned such that air flowing through the aerosol delivery device is incident upon the inlet apertures (e.g., the inlet apertures may extend substantially parallel to a longitudinal axis of the aerosol delivery device and hence substantially parallel to the airflow therethrough). Thus, the inlet apertures may assist in removing the vapor from the chamber. Baffles may additionally be positioned in and/or around the chamber in order to direct air into the chamber and/or direct the vapor out of the chamber.

Further, in some embodiments valves may be provided at one or both of the inlet apertures and the outlet apertures. Such valves may passively or actively open and close to allow flow of air into the chamber and/or allow flow of vapor out of the chamber. Alternatively or additionally, the inlet apertures and/or the outlet apertures may be particularly sized to provide a desired flow of the vapor from the chamber while ensuring substantially complete vaporization of the aerosol precursor composition.

In some embodiments, as illustrated in FIGS. 12 and 13, the atomizer 531 may additionally include a support member 533. The support member 533 may be configured to support the heating element 532 in a position adjacent an end of the fluid delivery tube 536 and, for example, co-linear therewith, so as to provide a smooth flow path. Further, the support member 533 may comprise an insulator or insulating material that insulates additional components of the cartridge 504 (e.g., the outer body 538) from heat produced by the heating element to substantially prevent damage thereto.

FIG. 14 illustrates a sectional view through an aerosol delivery device 600 according to an additional example embodiment of the present disclosure. As illustrated, the aerosol delivery device 600 may include a control body 602 and a cartridge 604. The control body 602 may include an indicator 606 (e.g., an LED), an electrical power source 608 (e.g., a battery, which may be rechargeable), a flow sensor 610, a motor assembly 612 comprising an actuator 614 and a rod 616, a piston 618, a valve assembly 620, a pump housing 622, a coupler 624, an atomizer 626 comprising a heating element 627, and an outer body 628. The cartridge 604 may include a base 630, a reservoir 632, a mouthpiece 634, and an outer body 636. The base 630 of the cartridge 604 may be configured to releasably engage the coupler 624 of the control body 602 to form a mechanical and electrical connection therebetween.

FIG. 15 illustrates an additional sectional view through the aerosol delivery device 600. More particularly, FIG. 15 illustrates a flow path of air through the aerosol delivery device 600 when a user draws on the mouthpiece 634. As illustrated, an airflow or flow of ambient air 638 may enter the aerosol delivery device 600 and travel past the flow sensor 610. Although the ambient air 638 is illustrated as flowing past the electrical power source 608, in other embodiments the air may not flow past the electrical power source and/or the flow sensor may be positioned at an alternative location. The air 638 may then travel through the coupler 624 through one or more apertures 640 defined therethrough, through the base 630, around the reservoir 632, and out the mouthpiece 634.

As illustrated in FIG. 15, in one embodiment the air 638 may enter the aerosol delivery device 600 through a longitudinal end thereof, opposite from the mouthpiece 634. However, in other embodiments the air may enter the aerosol delivery device at an alternate location. For example, the air may enter through the coupler or the base, or at a location between the base and the mouthpiece. Accordingly, it should be understood that the particular airflow patterns described herein are provided for example purposes only.

When the flow sensor 610 detects the puff, the motor assembly 612 may be actuated. In this regard, FIG. 16 illustrates an enlarged partial sectional view through the aerosol delivery device 600. The actuator 614 may be configured to linearly displace the rod 616. Accordingly, the motor assembly 612 may comprise a linear motor in some embodiments. By way of further example, in one embodiment the motor assembly 612 may comprise a SQUIGGLE motor as sold by New Scale Technologies, Inc. of Victor, N.Y. Such a motor may produce both linear and rotary movement of the rod 616.

When the motor assembly 612 is actuated, the actuator 614 may linearly displace the rod 616 in a first direction (e.g., to the left in terms of the orientation illustrated in FIG. 16) such that the piston 618 retracts away from the cartridge 604 further into the pump housing 622. As illustrated in FIG. 16, this movement may draw an aerosol precursor composition 642 through one or more one-way valves 644 of the valve assembly 620 into the pump housing 622.

Thereafter, the motor assembly 612 may be actuated such that the actuator 614 linearly displaces the rod 616 in a second direction (e.g., to the right in terms of the orientation illustrated in FIG. 16), opposite to the first direction, such that the piston 618 is directed toward the cartridge 604. Thereby, as illustrated in FIG. 17, the aerosol precursor composition 642 previously drawn into the pump housing 622 may be expelled to the atomizer 626. In this regard, the atomizer 626 may further comprise a fluid delivery tube 646. Thus, the aerosol precursor composition 642 may be directed through the fluid delivery tube 646 to the heating element 627. As illustrated, in one embodiment the fluid delivery tube 646 may be defined at least in part by the pump housing 622. Further, the atomizer 626 may comprise a housing 647 defining a chamber 649 in which the heating element 627 is positioned and to which the aerosol precursor composition 642 is delivered. Thus, issues with respect to the aerosol precursor composition 642 being directed into the air 638 and to a user without being vaporized may be avoided. In this regard, the aerosol precursor composition 642 may be directed into contact with the heating element 627 at the chamber 649 to ensure vaporization thereof.

In this regard, when the flow sensor 610 detects a puff on the aerosol delivery device 600, current from the electrical power source 608 may be directed to the heating element 627 to produce heat. Accordingly, the aerosol precursor composition 642 directed thereto may be heated and vaporized to define an aerosol or vapor 648 which exits the chamber 649 through one or more outlet apertures 651 defined in the housing 647. The vapor 648 may then mix with the air 638 and exit through the mouthpiece 634.

The chamber 649 (see, e.g., FIG. 16) may be configured to provide for optimal rates of release of the vapor 648 (see, e.g., FIG. 17) therefrom and into the air 638. In this regard, the outlet apertures 651 may be particularly sized and oriented so as to provide for a selected flow rate of the vapor 648 from the chamber 649. Although the outlet apertures 651 are illustrated as defining a round configuration, various other embodiments of outlet apertures such as non-circular apertures and/or a singular aperture may be employed in other embodiments.

Further, as illustrated in FIG. 16, in one embodiment the housing 647 may additionally define one or more inlet apertures 653 in communication with the chamber 649. The inlet apertures 653 may be configured to allow flow of air therethough into the chamber 649. Thus, as a user draws on the aerosol delivery device, air entering through the inlet apertures 653 may mix with the vapor 648 (see, e.g., FIG. 17) and exit through the outlet apertures 651. In this regard, the inlet apertures 653 may be positioned such that air flowing through the aerosol delivery device 600 is incident upon the inlet apertures (e.g., the inlet apertures may extend substantially parallel to a longitudinal axis of the aerosol delivery device and hence substantially parallel to the airflow therethrough). Thus, the inlet apertures 653 may assist in removing the vapor 648 from the chamber 649. Baffles may additionally be positioned in and/or around the chamber in order to direct air into the chamber and/or direct the vapor out of the chamber.

Further, in some embodiments valves may be provided at one or both of the inlet apertures and the outlet apertures. Such valves may passively or actively open and close to allow flow of air into the chamber and/or allow flow of vapor out of the chamber. Alternatively or additionally, the inlet apertures and/or the outlet apertures may be particularly sized to provide a desired flow of the vapor from the chamber while ensuring substantially complete vaporization of the aerosol precursor composition.

FIG. 18 illustrates a sectional view through an aerosol delivery device 700 according to an additional example embodiment of the present disclosure. As illustrated, the aerosol delivery device 700 may include a control body 702 and a cartridge 704. The control body 702 may include an indicator 706 (e.g., an LED), an electrical power source 708 (e.g., a battery, which may be rechargeable), a flow sensor 710, a motor assembly 712 comprising an actuator 714 and a rod 716, a piston 718, a valve assembly 720, a pump housing 722, a coupler 724, and an outer body 726. The cartridge 704 may include a base 728, a reservoir 730 that may include an aerosol precursor bag 732 received therein, an atomizer 733 comprising a heating element 734 and a fluid delivery tube 735, a mouthpiece 736, and an outer body 738. The base 728 of the cartridge 704 may be configured to releasably engage the coupler 724 of the control body 702 to form a mechanical and electrical connection therebetween.

FIG. 19 illustrates an additional sectional view through the aerosol delivery device 700. More particularly, FIG. 19 illustrates a flow path of air through the aerosol delivery device 700 when a user draws on the mouthpiece 736. As illustrated, an airflow or flow of ambient air 740 may enter the aerosol delivery device 700 and travel past the flow sensor 710. Although the ambient air 740 is illustrated as flowing past the electrical power source 708, in other embodiments the air may not flow past the electrical power source and/or the flow sensor may be positioned at an alternative location. The air 740 may then travel through the coupler 724 through one or more apertures 742 defined therethrough, through the base 728, around the reservoir 730, and out the mouthpiece 736.

As illustrated in FIG. 19, in one embodiment the air 740 may enter the aerosol delivery device 700 through a longitudinal end thereof, opposite from the mouthpiece 736. However, in other embodiments the air may enter the aerosol delivery device at an alternate location. For example, the air may enter through the coupler or the base, or at a location between the base and the mouthpiece. Accordingly, it should be understood that the particular airflow patterns described herein are provided for example purposes only.

When the flow sensor 710 detects the puff, the motor assembly 712 may be actuated. In this regard, FIG. 20 illustrates an enlarged partial sectional view through the aerosol delivery device 700. The actuator 714 may be configured to linearly displace the rod 716. Accordingly, the motor assembly 712 may comprise a linear motor in some embodiments. By way of further example, in one embodiment the motor assembly 712 may comprise a SQUIGGLE motor as sold by New Scale Technologies, Inc. of Victor, N.Y. Such a motor may produce both linear and rotary movement of the rod 714.

When the motor assembly 712 is actuated, the actuator 714 may linearly displace the rod 716 in a first direction (e.g., to the right in terms of the orientation illustrated in FIG. 20) such that the piston 718 is directed toward the cartridge 704. The piston 718 may displace air (or another fluid) from the pump housing 722 and through the valve assembly 720. Thus, the air may enter the reservoir 730 and apply pressure to the aerosol precursor bag 732 to dispense an aerosol precursor composition 744 as discussed below.

Use of the aerosol precursor bag 732, as opposed to a rigid container, may assist in dispensing the aerosol precursor composition 744 from the reservoir 730. In this regard, the aerosol precursor bag 732 may shrink or deform as the aerosol precursor composition 744 is dispensed therefrom, whereas use of a rigid container may resist deformation and thereby not dispense the aerosol precursor composition. In one embodiment the aerosol precursor bag 732 may comprise an elastomeric material (e.g., rubber).

Regardless of the particular embodiment of reservoir employed, as illustrated in FIG. 20, the aerosol precursor composition 744 retained in the aerosol precursor bag 732 may be expelled to the atomizer 733. In particular, the aerosol precursor composition 744 may be directed through the fluid delivery tube 735 to the heating element 734. Further, the atomizer 733 may comprise a housing 745 defining a chamber 747 in which the heating element 734 is positioned and to which the aerosol precursor composition 744 is delivered. Thus, issues with respect to the aerosol precursor composition 744 being directed into the air 740 and to a user without being vaporized may be avoided. In this regard, the aerosol precursor composition 744 may be directed into contact with the heating element 734 at the chamber 747 to ensure vaporization thereof.

In this regard, when the flow sensor 710 detects a puff on the aerosol delivery device 700, current from the electrical power source 708 may be directed to the heating element 734 to produce heat. Accordingly, the aerosol precursor composition 744 directed thereto may be heated and vaporized to define an aerosol or vapor 748 which exits the chamber 747 through one or more outlet apertures 749 defined in the housing 745. The vapor 748 may then mix with the air 740 and exit through the mouthpiece 736.

The chamber 747 (see, e.g., FIG. 20) may be configured to provide for optimal rates of release of the vapor 748 therefrom and into the air 740. In this regard, the outlet apertures 749 may be particularly sized and oriented so as to provide for a selected flow rate of the vapor 748 from the chamber 747. Although the outlet apertures 749 are illustrated as defining a round configuration, various other embodiments of outlet apertures such as non-circular apertures and/or a singular aperture may be employed in other embodiments.

Further, in one embodiment the atomizer may additionally define one or more inlet apertures in communication with the chamber. The inlet apertures may be configured to allow flow of air therethough into the chamber. Thus, as a user draws on the aerosol delivery device, air entering through the inlet apertures may mix with the vapor and exit through the outlet aperture(s). In this regard, the inlet apertures may be positioned such that air flowing through the aerosol delivery device is incident upon the inlet apertures (e.g., the inlet apertures may extend substantially parallel to a longitudinal axis of the aerosol delivery device and hence substantially parallel to the airflow therethrough). Thus, the inlet apertures may assist in removing the vapor from the chamber. Baffles may additionally be positioned in and/or around the chamber in order to direct air into the chamber and/or direct the vapor out of the chamber.

Further, in some embodiments valves may be provided at one or both of the inlet apertures and the outlet apertures. Such valves may passively or actively open and close to allow flow of air into the chamber and/or allow flow of vapor out of the chamber. Alternatively or additionally, the inlet apertures and/or the outlet apertures may be particularly sized to provide a desired flow of the vapor from the chamber while ensuring substantially complete vaporization of the aerosol precursor composition.

After dispensing, the actuator 714 of the motor assembly 712 may retract the piston 718 away from the cartridge 704 further into the pump housing 722 in a second direction (e.g., to the left in terms of the orientation illustrated in FIG. 20), opposite to the first direction. One or more one-way valves 750 of the valve assembly 720 may prevent air from being drawn out of the reservoir 730 during this movement. Accordingly, the piston 718 may be returned to the retracted position, where it may remain until another puff on the aerosol delivery device 700 is detected by the flow sensor 710. In an alternate embodiment of the aerosol delivery device 700, the motor assembly may employ mechanical force (e.g., by contacting the aerosol precursor bag with the rod or the piston) to directly expel the aerosol precursor composition from the aerosol precursor bag.

FIG. 21 illustrates an exploded view of an aerosol delivery device 1000 according to an additional example embodiment of the present disclosure. As illustrated, the aerosol delivery device 1000 may include a control body 1002 and a cartridge 1004. The control body 1002 may include an indicator 1006 (e.g., an LED), a circuit or circuit board 1008, an electrical power source 1010 (e.g., a battery, which may be rechargeable), a flow sensor 1012, an atomizer 1014, wiring 1016, a pump housing 1018, a pump 1020 (e.g., a piezoelectric pump sold by MicroFab Technologies, Inc. of Plano, Tex.), a coupler 1022, and an outer body 1024. The cartridge 1004 may include a base 1026, a reservoir 1028, a lid 1030 that encloses the reservoir, a mouthpiece 1032, and an outer body 1034. The base 1026 of the cartridge 1004 may be configured to releasably engage the coupler 1022 of the control body 1002 to form a mechanical and electrical connection therebetween.

FIG. 22 illustrates a modified sectional view through the aerosol delivery device 1000. More particularly, FIG. 22 illustrates a flow path of air through the aerosol delivery device 1000 when a user draws on the mouthpiece 1032. As illustrated, an airflow or flow of ambient air 1036 may enter the aerosol delivery device 1000 and travel past the flow sensor 1012. The air 1036 may then travel around the atomizer 1014 and the pump housing 1018, through the coupler 1022 through one or more apertures 1038 defined therethrough, through the base 1026, around the reservoir 1028, and out the mouthpiece 1032.

As illustrated in FIG. 22, in one embodiment the air 1036 may enter the aerosol delivery device 1000 through the outer body 1024 (e.g., through one or more apertures defined therein). However, in other embodiments the air may enter the aerosol delivery device at an alternate location. For example, the air may enter through a longitudinal end of the aerosol delivery device opposite from the mouthpiece, though the coupler or the base, or at a location between the base and the mouthpiece. Accordingly, it should be understood that the particular airflow patterns described herein are provided for example purposes only.

When the flow sensor 1012 detects the puff, the pump 1020 may be actuated. In this regard, as illustrated in FIG. 22, the coupler 1022 may include a receptacle 1040 configured to receive and hold the pump 1020. Accordingly, as illustrated in FIG. 22, when the control body 1002 is coupled to the cartridge 1004, the pump 1020 may engage the reservoir 1028.

As illustrated in FIG. 23, when the pump 1020 is actuated, an aerosol precursor composition 1042 in the reservoir 1028 may be pumped toward the atomizer 1014. In this regard, the pump 1020 may include a driver device configured to produce a pressure wave that forces the aerosol precursor composition 1042 therethrough. In this regard, in some embodiments the driver device may comprise a piezoelectric actuator described, by way of example, in U.S. Pat. No. 5,053,100 to Hayes et al., which is incorporated herein by reference in its entirety. FIG. 24 illustrates an enlarged modified sectional view of the atomizer 1014. As illustrated, the atomizer 1014 may include a fluid delivery tube 1044, a heating element 1046, and a cap 1048. The fluid delivery tube 1044 may include an aperture 1050 configured to receive the aerosol precursor composition 1042 from the pump 1020 and direct the aerosol precursor composition to the heating element 1046.

FIG. 25 illustrates an opposing enlarged partial perspective view of the heating element 1046 and the cap 1048. When the flow sensor 1012 detects a puff on the aerosol delivery device 1000, current from the electrical power source 1008 may be directed to the heating element 1046 to produce heat. For example, current may be directly delivered to the heating element 1046, or current may directed to terminals coupled to the heating element. Accordingly, the aerosol precursor composition 1042 directed through the aperture 1050 in the fluid delivery tube 1044 may be heated and vaporized by the heating element 1046 to define an aerosol or vapor 1052. In one embodiment the fluid delivery tube 1044 and the cap 1048 may cooperatively define a chamber 1051 (see, FIG. 22) in which the heating element 1046 is positioned and to which the aerosol precursor composition 1042 is delivered. Thus, issues with respect to the aerosol precursor composition 1042 being directed into the air 1036 and to a user without being vaporized may be avoided. In this regard, the aerosol precursor composition 1042 may be directed into contact with the heating element 1046 at the chamber 1051 to ensure vaporization thereof. The vapor 1052 (see, FIG. 23) may then exit the atomizer 1014 through radially extending grooves 1054 in the cap 1048 (see, FIG. 25) and intermix and travel with the air 1036 to the mouthpiece 1032.

The chamber 1051 (see, FIG. 22) may be configured to provide for optimal rates of release of the vapor 1052 therefrom and into the air 1036. In this regard, the radially extending grooves 1054 defined in the cap may be particularly sized and oriented so as to provide for a selected flow rate of the vapor 1052 (see, FIG. 23) from the chamber 1051. Although grooves are described above as being employed to allow for outflow of vapor from the chamber, various other embodiments of outlet apertures such as one or more round holes may be employed in other embodiments.

Further, in one embodiment the housing may additionally define one or more inlet apertures in communication with the chamber. The inlet apertures may be configured to allow flow of air therethough into the chamber. Thus, as a user draws on the aerosol delivery device, air entering through the inlet apertures may mix with the vapor and exit through the outlet apertures (e.g., the grooves). In this regard, the inlet apertures may be positioned such that air flowing through the aerosol delivery device is incident upon the inlet apertures (e.g., the inlet apertures may extend substantially parallel to a longitudinal axis of the aerosol delivery device and hence substantially parallel to the airflow therethrough). Thus, the inlet apertures may assist in removing the vapor from the chamber. Baffles may additionally be positioned in and/or around the chamber in order to direct air into the chamber and/or direct the vapor out of the chamber.

Further, in some embodiments valves may be provided at one or both of the inlet apertures and the outlet apertures. Such valves may passively or actively open and close to allow flow of air into the chamber and/or allow flow of vapor out of the chamber. Alternatively or additionally, the inlet apertures and/or the outlet apertures may be particularly sized to provide a desired flow of the vapor from the chamber while ensuring substantially complete vaporization of the aerosol precursor composition.

FIG. 26 illustrates a sectional view through an aerosol delivery device 1100 according to an additional example embodiment of the present disclosure. As illustrated, the aerosol delivery device 1100 may include a control body 1102 and a cartridge 1104. The control body 1102 may include an indicator 1106 (e.g., an LED), an electrical power source 1108 (e.g., a battery, which may be rechargeable), a flow sensor 1110, a coupler 1112, and an outer body 1114. The cartridge 1104 may include a base 1116, an atomizer 1118 (e.g., comprising a heating element 1119), a pump 1120 (e.g., a micropump on a silicon chip as sold by Debiotech of Lausanne, Switzerland), a reservoir 1122, a lid 1124 that encloses the reservoir, a mouthpiece 1126, and an outer body 1128. The base 1116 of the cartridge 1104 may be configured to releasably engage the coupler 1112 of the control body 1102 to form a mechanical and electrical connection therebetween.

FIG. 27 illustrates an additional sectional view through the aerosol delivery device 1100. More particularly, FIG. 27 illustrates a flow path of air through the aerosol delivery device 1100 when a user draws on the mouthpiece 1126. As illustrated, an airflow or flow of ambient air 1130 may enter the aerosol delivery device 1100 and travel past the flow sensor 1110. Although the ambient air 1130 is illustrated as flowing past the electrical power source 1108, in other embodiments the air may not flow past the electrical power source and/or the flow sensor may be positioned at an alternative location. The air 1130 may then travel through the coupler 1112 through one or more apertures 1132 defined therethrough, through the base 1116, around the atomizer 1118 and the reservoir 1122, and out the mouthpiece 1126.

As illustrated in FIG. 27, in one embodiment the air 1130 may enter the aerosol delivery device 1100 through a longitudinal end thereof, opposite from the mouthpiece 1126. However, in other embodiments the air may enter the aerosol delivery device at an alternate location. For example, the air may enter through the coupler or the base, or at a location between the base and the mouthpiece. Accordingly, it should be understood that the particular airflow patterns described herein are provided for example purposes only.

FIG. 28 illustrates an enlarged partial sectional view of the aerosol delivery device 1100. When the flow sensor 1110 detects the puff, current may be applied to the pump 1120. Thereby, an aerosol precursor composition 1134 retained in the reservoir 1122 may be expelled toward the atomizer 1118. The atomizer 1118 may further comprise a housing 1133 defining a chamber 1135 in which the heating element 1119 is positioned and to which the aerosol precursor composition 1134 is delivered. Thus, issues with respect to the aerosol precursor composition 1134 being directed into the air 1130 and to a user without being vaporized may be avoided. In this regard, the aerosol precursor composition 1134 may be directed into contact with the heating element 1119 at the chamber 1135 to ensure vaporization thereof.

In this regard, when the flow sensor 1110 detects a puff on the aerosol delivery device 1100, current from the electrical power source 1108 may be directed to the heating element 1119 to produce heat. Accordingly, the aerosol precursor composition 1134 directed thereto may be heated and vaporized to define an aerosol or vapor 1136. The resulting vapor 1136 may then exit the chamber 1135 through one or more outlet apertures 1137, mix with the air 1130, and exit through the mouthpiece 1126.

The chamber 1135 (see, e.g., FIG. 28) may be configured to provide for optimal rates of release of the vapor 1136 therefrom and into the air 1130. In this regard, the outlet apertures 1137 may be particularly sized and oriented so as to provide for a selected flow rate of the vapor 1136 from the chamber 1135. Although the outlet apertures 1137 are illustrated as defining a round configuration, various other embodiments of outlet apertures such as non-circular apertures and/or a singular aperture may be employed in other embodiments.

Further, in one embodiment the atomizer may additionally define one or more inlet apertures in communication with the chamber. The inlet apertures may be configured to allow flow of air therethough into the chamber. Thus, as a user draws on the aerosol delivery device, air entering through the inlet apertures may mix with the vapor and exit through the outlet aperture(s). In this regard, the inlet apertures may be positioned such that air flowing through the aerosol delivery device is incident upon the inlet apertures (e.g., the inlet apertures may extend substantially parallel to a longitudinal axis of the aerosol delivery device and hence substantially parallel to the airflow therethrough). Thus, the inlet apertures may assist in removing the vapor from the chamber. Baffles may additionally be positioned in and/or around the chamber in order to direct air into the chamber and/or direct the vapor out of the chamber.

Further, in some embodiments valves may be provided at one or both of the inlet apertures and the outlet apertures. Such valves may passively or actively open and close to allow flow of air into the chamber and/or allow flow of vapor out of the chamber. Alternatively or additionally, the inlet apertures and/or the outlet apertures may be particularly sized to provide a desired flow of the vapor from the chamber while ensuring substantially complete vaporization of the aerosol precursor composition.

In the various embodiments of aerosol delivery devices described above, connectors between the cartridge and control body allow for fluid dispensing to an atomizer and additionally provide an electrical connection therebetween, such that, for example, power from an electrical power source may be provided to the atomizer. For example, in the aerosol delivery device 400 illustrated in FIGS. 2-9, the base and coupler are configured such that a rod may extend from the control body through the coupler and the base to displace a piston in the cartridge. Further, the aerosol delivery devices 500, 600, 700, 1000, 1100 illustrated in FIGS. 10-28 include connections configured to direct the aerosol precursor composition therethrough. In particular the aerosol precursor composition is directed from the cartridge through the base and into the control body through the coupler. The connectors may also be configured to allow for airflow therethrough. For example, the cartridge may be configured to receive an airflow from the control body through the coupler and the base.

Note that various embodiments of atomizers may be employed to vaporize the aerosol precursor composition in the embodiments of aerosol delivery devices described above. Such atomizers may include flat heaters, wound wire surfaces, micro heaters (e.g., embodied on a chip) glass plates, lasers, resistive heaters, and any other shape and embodiment of heater. Further, the materials employed in the first heating elements and the second heating elements may vary. For example, the materials described above with respect to wire coil heating elements may be employed. Various other materials which may be employed in the heating elements described herein may include platinum or a platinum-coated materials and resistive inks (e.g., printed on a ceramic material).

Certain aerosol delivery devices described herein may avoid certain issues associated with conventional aerosol delivery devices that employ a wick. In this regard, use of a wick may cause separation of the ingredients of an aerosol precursor composition. Further, use of a wick to transfer the aerosol precursor composition from a substrate to a heating element may result in leakage. Accordingly, the embodiments of the aerosol delivery devices disclosed herein may provide these and/or other advantages.

Note that while the aerosol delivery devices disclosed herein are generally described as including a cartridge (e.g., a replaceable cartridge) and a control body (e.g., a reusable control body), various other embodiments may be employed. For example, in other embodiments the aerosol delivery devices may include more than two-pieces. In an additional embodiment the aerosol delivery device may define an integral, one-piece configuration.

Although the present disclosure includes various example embodiments that have generally been described separately, it should be understood that elements and components of each of the various embodiments disclosed herein are interchangeable. Thus, this disclosure is intended to be read holistically such that any separable features or elements of the disclosed invention, in any of its various aspects and embodiments, should be viewed as intended to be combinable unless the context clearly dictates otherwise.

In an additional embodiment, a method for aerosolization in an aerosol delivery device is provided. As illustrated in FIG. 29, the method may include directing an airflow from a control body through a cartridge comprising a reservoir at least partially filled with an aerosol precursor composition at operation 1402. Further, the method may include dispensing the aerosol precursor composition from the reservoir to an atomizer comprising a heating element with a positive displacement apparatus at operation 1404. The method may additionally include heating the aerosol precursor composition dispensed from the reservoir with the heating element to produce an aerosol at operation 1406.

In some embodiments dispensing the aerosol precursor composition at operation 1404 may comprise displacing a piston within a pump housing with an actuator. In this regard, a motor assembly including, for example, the actuator and a rod may displace the piston. In some embodiments the actuator may comprise a linear motor in some embodiments. By way of further example, in one embodiment the motor assembly may comprise a SQUIGGLE motor as sold by New Scale Technologies, Inc. of Victor, N.Y. Such a motor may produce both linear and rotary movement of the rod. Further, displacing the piston within the pump housing may comprise displacing the piston within the reservoir. In other words, the reservoir may define the pump housing.

In an additional embodiment displacing the piston within the pump housing may comprise displacing a fluid from the pump housing into the reservoir. Displacing the fluid from the pump housing into the reservoir may comprise displacing the aerosol precursor composition from an aerosol precursor bag in the reservoir. Further, displacing the piston within the pump housing may comprise moving the piston in a first direction to draw the aerosol precursor composition from the reservoir into the pump housing and moving the piston in an opposing second direction to direct the aerosol precursor composition from the pump housing to the atomizer. Additionally, the method may include preventing flow of the aerosol precursor composition from the atomizer to the pump housing and preventing flow of the aerosol precursor composition from the pump housing to the reservoir with a valve assembly.

In some embodiments dispensing the aerosol precursor composition from the reservoir to the atomizer at operation 1404 may comprise delivering the aerosol precursor composition through a fluid delivery tube to the heating element. Delivering the aerosol precursor composition through the fluid delivery tube to the heating element may comprise delivering the aerosol precursor composition to a groove defined in an end of the fluid delivery tube. Further, heating the aerosol precursor composition at operation 1406 may comprise heating the aerosol precursor composition in the groove. Additionally, heating the aerosol precursor composition at operation 1406 may comprise heating the aerosol precursor composition in a chamber.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

What is claimed is:

1. An aerosol delivery device, comprising:
a control body;
a cartridge comprising a reservoir at least partially filled with an aerosol precursor composition, the cartridge being configured to receive an airflow from the control body;
a positive displacement apparatus configured to dispense the aerosol precursor composition from the reservoir; and
an atomizer comprising a heating element configured to heat the aerosol precursor composition received from the reservoir to add a vapor to the airflow and form an aerosol.

2. The aerosol delivery device of claim 1, wherein the positive displacement apparatus comprises an actuator, a piston, and a pump housing, the actuator being configured to displace the piston within the pump housing to dispense the aerosol precursor composition from the reservoir.

3. The aerosol delivery device of claim 2, wherein the reservoir comprises the pump housing.

4. The aerosol delivery device of claim 2, wherein the piston is configured to displace a fluid from the pump housing into the reservoir.

5. The aerosol delivery device of claim 4, wherein the reservoir comprises an aerosol precursor bag.

6. The aerosol delivery device of claim 2, wherein the actuator is configured to move the piston in a first direction to draw the aerosol precursor composition from the reservoir into the pump housing and configured to move the piston in an opposing second direction to direct the aerosol precursor composition from the pump housing to the atomizer.

7. The aerosol delivery device of claim 6, further comprising a valve assembly configured to be positioned between the pump housing and the reservoir.

8. The aerosol delivery device of claim 1, wherein the atomizer further comprises a fluid delivery tube configured to deliver the aerosol precursor composition to the heating element.

9. The aerosol delivery device of claim 8, wherein a groove defined in an end of the fluid delivery tube is configured to receive the aerosol precursor composition, and
wherein the heating element defines at least one of a size, a shape, and a pattern that substantially matches the groove.

10. The aerosol delivery device of claim 1, wherein the atomizer further comprises at least one of a heater disk and a cap, the heating element being coupled to, imbedded in, or printed on the heater disk or the cap.

11. The aerosol delivery device of claim 1, wherein the heating element defines a tubular configuration.

12. The aerosol delivery device of claim 11, wherein the atomizer further comprises a fluid delivery tube that is adjacent to and co-linear with the heating element.

13. The aerosol delivery device of claim 1, wherein the atomizer defines a chamber and the heating element is positioned within the chamber.

14. The aerosol delivery device of claim 1, comprising at least two one-way valves opening in opposing directions to alternatively allow the aerosol precursor composition out of the reservoir and into the atomizer.

15. An aerosol delivery device, comprising:
a cartridge comprising a base and a reservoir at least partially filled with an aerosol precursor composition; and
a control body comprising a coupler, the base and the coupler being configured to direct the aerosol precursor composition from the reservoir therethrough to an atomizer comprising a heating element configured to heat the aerosol precursor composition received from the reservoir to form a vapor, wherein the cartridge is configured to receive an airflow from the control body through the coupler and the base.

16. The aerosol delivery device of claim 15, wherein the control body further comprises an electrical power source, the base and the coupler being configured to form an electrical connection therebetween.

17. The aerosol delivery device of claim 15, further comprising a positive displacement apparatus configured to dispense the aerosol precursor composition from the reservoir through the base and the coupler to the atomizer.

18. A method for aerosolization in an aerosol delivery device, comprising:
   directing an airflow from a control body through a cartridge comprising a reservoir at least partially filled with an aerosol precursor composition;
   dispensing the aerosol precursor composition from the reservoir to an atomizer comprising a heating element with a positive displacement apparatus; and
   heating the aerosol precursor composition dispensed from the reservoir with the heating element to produce an aerosol.

19. The method of claim 18, wherein dispensing the aerosol precursor composition comprises displacing a piston within a pump housing with an actuator.

20. The method of claim 19, wherein displacing the piston within the pump housing comprises displacing the piston within the reservoir.

21. The method of claim 19, wherein displacing the piston within the pump housing comprises displacing a fluid from the pump housing into the reservoir.

22. The method of claim 21, wherein displacing the fluid from the pump housing into the reservoir comprises displacing the aerosol precursor composition from an aerosol precursor bag in the reservoir.

23. The method of claim 19, wherein displacing the piston within the pump housing comprises moving the piston in a first direction to draw the aerosol precursor composition from the reservoir into the pump housing and moving the piston in an opposing second direction to direct the aerosol precursor composition from the pump housing to the atomizer.

24. The method of claim 23, further comprising preventing flow of the aerosol precursor composition from the atomizer to the pump housing and preventing flow of the aerosol precursor composition from the pump housing to the reservoir with a valve assembly.

25. The method of claim 18, wherein dispensing the aerosol precursor composition from the reservoir to the atomizer comprises delivering the aerosol precursor composition through a fluid delivery tube to the heating element.

26. The method of claim 25, wherein delivering the aerosol precursor composition through the fluid delivery tube to the heating element comprises delivering the aerosol precursor composition to a groove defined in an end of the fluid delivery tube, and
   wherein heating the aerosol precursor composition comprises heating the aerosol precursor composition in the groove.

27. The method of claim 18, wherein heating the aerosol precursor composition comprises heating the aerosol precursor composition in a chamber.

* * * * *